United States Patent
Rampersad

(10) Patent No.: US 8,068,104 B2
(45) Date of Patent: Nov. 29, 2011

(54) TOTALLY INTEGRATED INTELLIGENT DYNAMIC SYSTEMS DISPLAY

(76) Inventor: Carlyle Rampersad, Seattle, WA (US)

( * ) Notice: Subject to any disclaimer, the term of this patent is extended or adjusted under 35 U.S.C. 154(b) by 847 days.

(21) Appl. No.: 12/132,797

(22) Filed: Jun. 4, 2008

(65) Prior Publication Data

US 2009/0046096 A1 Feb. 19, 2009

Related U.S. Application Data

(60) Provisional application No. 60/976,897, filed on Oct. 2, 2007, provisional application No. 60/937,655, filed on Jun. 29, 2007.

(51) Int. Cl.
| | |
|---|---|
| G06T 11/20 | (2006.01) |
| G06T 15/00 | (2006.01) |
| G06F 19/00 | (2006.01) |
| G06F 11/30 | (2006.01) |
| G01M 17/00 | (2006.01) |
| G01B 3/00 | (2006.01) |
| G01B 3/44 | (2006.01) |
| G01B 5/28 | (2006.01) |
| A61B 5/00 | (2006.01) |

(52) U.S. Cl. .......... 345/440; 345/419; 700/108; 701/29; 702/33; 702/34; 702/35; 702/182; 702/183; 600/301

(58) Field of Classification Search ............ 345/440, 345/440.1, 440.2, 418, 419; 700/29–32, 700/108–110; 701/29–35
See application file for complete search history.

(56) References Cited

U.S. PATENT DOCUMENTS

| | | | |
|---|---|---|---|
| 5,661,668 A | 8/1997 | Yemini | |
| 5,845,002 A | 12/1998 | Heck | |
| 6,157,864 A | 12/2000 | Schwenke | |
| 7,266,781 B1 * | 9/2007 | Burlowski | 715/834 |
| 7,702,437 B2 * | 4/2010 | Gilbert | 701/29 |
| 2001/0047691 A1 * | 12/2001 | Dzenis | 73/587 |
| 2002/0123976 A1 * | 9/2002 | Baar | 706/11 |
| 2002/0152150 A1 * | 10/2002 | Cooper et al. | 705/36 |
| 2004/0037230 A1 * | 2/2004 | Kroboth et al. | 370/252 |
| 2006/0173268 A1 | 8/2006 | Mullick | |
| 2006/0241510 A1 * | 10/2006 | Halperin et al. | 600/534 |
| 2008/0262795 A1 * | 10/2008 | Webb et al. | 702/184 |
| 2009/0157248 A1 * | 6/2009 | Gilbert | 701/29 |
| 2010/0238175 A1 * | 9/2010 | Gilbert | 345/440 |

OTHER PUBLICATIONS

Powsner, Tufte, Graphical Summary of Patient Status, Aug. 6, 1994, 386-389, The Lancet, US and UK.
Ordonez, et al., Visualizing Multivariate Time Series Data to Detect Specific Medical Conditions, AMIA 2008 Symposium Proceedings, pp. 530-534.

* cited by examiner

*Primary Examiner* — Xiao Wu
*Assistant Examiner* — Andrew Shin
(74) *Attorney, Agent, or Firm* — Virginia P. Shogren

(57) ABSTRACT

An apparatus for graphically displaying analytical data, comprising a generic model to graphically represent a complex set of physical characteristics potentially leading to catastrophic failure of a physical system. A central region represents failure of the physical system; a series of concentric ridges represents level of function. Wedge shaped regions upon the ridges represent predetermined subsystems of the physical system. An icon is displayed with changes in the icon proportional to time, and any one or more of color, position, shape, and rotation of the icon representing prescribed analysis of the physical characteristics. Mappings correlate predetermined characteristics of the system with failure of the physical system, levels of functioning represented by the ridges, subsystems represented by the wedge shaped regions, and/or analysis of the physical characteristics represented in the icon. A sensor interface receives measurements, and a graphics generator prepares a presentation of the model.

27 Claims, 18 Drawing Sheets

FIG.9A

| Renal System Tests<br>Primary testing | Percentages Generated | Percentages Assigned | Normal Values | Current Values | Patient & Disease Specific Values | Calculated Function |
|---|---|---|---|---|---|---|
| BUN | | | | | | |
| Creatinine, serum | | | | | | |
| CBC | | | | | | |
| Hemoglobin | | | | | | |
| HCT | | | | | | |
| MPV | | | | | | |
| Serum Chemistry | | | | | | |
| Profile-CMP | | | | | | |
| BUN | | | | | | |
| Creatine | | | | | | |
| Electrolytes | | | | | | |
| Na | | | | | | |
| K | | | | | | |
| Cl | | | | | | |
| CO2 | | | | | | |
| Globulin | | | | | | |
| Electrolytes, serum | | | | | | |
| Na | | | | | | |
| K | | | | | | |
| Cl | | | | | | |
| CO2 | | | | | | |
| Bicarbonate, serum | | | | | | |
| Magnesium, serum | | | | | | |
| Phosphorus, serum | | | | | | |
| Adults < 60 | | | | | | |
| Female > 60 | | | | | | |
| Adults > 60 | | | | | | |
| Globulin, serum | | | | | | |
| Uric Acid, serum | | | | | | |
| Adult Female | | | | | | |
| Adult Male | | | | | | |
| Panic | | | | | | |
| Urinalysis | | | | | | |
| Albumin | | | | | | |
| Appearance | | | | | | |
| Bilirubin | | | | | | |
| Color | | | | | | |
| Glucose | | | | | | |
| Ketones | | | | | | |

| | | | | | | | |
|---|---|---|---|---|---|---|---|
| | Nitrite | | | | | | |
| | Occult Blood | | | | | | |
| | pH | | | | | | |
| | Odor | | | | | | |
| | Protein | | | | | | |
| | Spec Gravity | | | | | | |
| | Urobilinogen | | | | | | |
| | Cells | | | | | | |
| | Ery | | | | | | |
| | Leuk | | | | | | |
| | Other | | | | | | |
| | Epith | | | | | | |
| | Casts | | | | | | |
| | Crystal | | | | | | |
| | Bacteria | | | | | | |
| | Parasite | | | | | | |
| | Calcium, serum | | | | | | |
| | Uric Acid, serum | | | | | | |
| | Beta2 Microgibulin, blood & 24 h urine | | | | | | |
| | Immunoelectrophoresis, serum & urine | | | | | | |
| | Myoglobin, serum | | | | | | |
| | Myoglobin, serum Qualitative urine | | | | | | |
| | Transferrin, serum | | | | | | |
| | Aldosterone, serum and urine | | | | | | |
| | Renin, blood | | | | | | |
| | CreatineKinase | | | | | | |
| | CreatineKinaseIsoenzyme | | | | | | |
| | LDH, blood | | | | | | |
| | LDH Isoenzyme, blood | | | | | | |
| | Occult blood, urine | | | | | | |
| | Oxalate, 24 h urine | | | | | | |
| | pH, urine | | | | | | |
| | Cystine, qualitative urine | | | | | | |
| | Kidney stone analysis | | | | | | |
| | Histopathology, specimen | | | | | | |
| | Diagnostic Procedures | | | | | | |
| | KUB radiograph | | | | | | |
| | kidney Sonogram | | | | | | |
| | Kidney Biopsy | | | | | | |
| | CT | | | | | | |
| | IVP Nephrotomography | | | | | | |
| | Renal Angiogram | | | | | | |
| | MRI | | | | | | |
| | Lithotripsy | | | | | | |

Patient:    Date:    Time:    Total Function ☐

*FIG. 9B*

Total cardiovascular function level 30 + 18 + 6 = 54%

TOTALLY INTEGRATED INTELLIGENT DYNAMIC SYSTEMS DISPLAY

CROSS REFERENCE TO RELATED APPLICATIONS

This application claims priority under 35 USC 119(e) of Provisional Patent Application Ser. No. 60/976,897 filed Oct. 2, 2007, entitled "Totally Integrated Interactive Patient Systems Display," and Provisional Patent Application Ser. No. 60/937,655 filed Jun. 29, 2007, entitled "Totally Integrated Intelligent Dynamic Systems Display" which are hereby incorporated by reference in their entirety.

FIELD OF THE INVENTION

The invention relates to dynamic systems analysis and displays for complex entities comprising one or more system or subsystems, and particularly, to a three-dimensional dynamic error model for visual display of the status of the multiple subsystems in real time.

BACKGROUND OF THE INVENTION

System Dynamics

Over any period of time, in any complex system, there are two forces working in opposite directions. One force is working to maintain the unit at optimum function under the theory of complexity. Working in opposition to this force is the force of entropy. The role of a person overseeing the complex system, such as a physician for the patient, is to maintain and manage this complex system within the environment in which the system is operating. Left alone, without any input, the system will eventually collapse. The patient in the hospital will eventually deteriorate after the body's natural compensating mechanisms have failed. The relationship within the multiple subsystems, if observed over a period of time, can alert the educated observer of specific patterns or trends which can give an early warning of impending failure or potentially developing complications. Without this advantage, making decisions which are reactive, instead of proactive, can lead to errors in judgment and, potentially, catastrophic or adverse outcomes.

Existing Methods for Analyzing Errors

Adverse outcomes are typically analyzed from the perspective of a series of separate events linked as though the events are part of a chain. Under the "chain of events" theory, a break in any of the links in the chain prevents the error, accident, or other catastrophic event. This approach to analyzing accidents is flawed since each link is viewed as contributing to the outcome, but breaking a link does not necessarily stop or prevent the accident. In addition, this theory does not address the concept of time within the chain of events.

Another method for analyzing adverse events is referred to as the "swiss cheese" model. Under the "swiss cheese" model, different outcomes can be represented by vertically oriented, spaced panel-shaped ridges with holes in the ridges at different positions. When the ridges are positioned such that one or more holes line up, errors are allowed to progress through the system leading to adverse events. The "swiss cheese" model also is flawed for reasons including an infinite number of ridges are required to stop all errors; it does not address the concept of time; it does not explain where the error comes from, and it does not explain where the error goes when it is stopped.

Error Analysis in Natural/Complex Systems

Natural systems, such as the human body, have compensating mechanisms to prevent errors or catastrophic failures. The compensating mechanism in natural systems makes providing trend analysis even more important to prevent outright catastrophic failures. For example, if a patient has blocked coronary arteries, the body compensates by developing collateral circulation, and thus the patient is unaware of the cardiovascular disease until the demands for more oxygenated blood in a high work environment results in the circulation being unable to supply the heart muscle with oxygenated blood. The end result is a heart attack.

Error analysis leading to catastrophes in other complex systems, such as airline crashes, is an evolving area of study. Forty years ago, boarding a commercial airplane was a risky proposition. Arriving safely at the intended destination was not guaranteed. In 1960 alone, a major airline crash occurred in the US almost monthly. As these accidents were studied in an effort to improve safety records, four reasons emerged as to the root causes of these disasters: 1) a catalyst event; 2) a system fault; 3) loss of situational awareness; and, 4) human error. The airlines, the aircraft manufacturers, the Federal Aviation Administration (FAA) and the Airline Pilots Association have focused on 4 major areas to prevent airline disasters: 1) improving the technologies on board airliners and in the air traffic control system; 2) proficiency (initial and recurrent) training for flight crews; 3) the development of Standard Operating Procedures for all phases of flight; and, 4) developing understanding of the critical role human factors play in the exercise of proper judgment.

Medicine, like aviation, is a 'high reliability organization'. A high reliability organization is any organization where a high degree of functioning reliability is required to fulfill its intended purpose. The margin for error is small. Even the slightest error can have catastrophic and costly results.

Postmortem analysis of disasters—whether the disaster is in the field of medicine, aviation, or other complex systems—has shown that human factors lie at the root of most major disasters. And while there exist various models for error analysis after the error has occurred, there is long felt, unsatisfied need for systems that both openly address human frailty and provide humans with the information they need (despite themselves) to act correctly in a disaster scenario. Accordingly, there is a need in the art for a dynamic error model that provides readily visible information about the status and condition of complex systems over time, which takes into account and mitigates against the human factors at the root of disasters, and which can present accurate, real-time information to evaluate, provide trend analysis, and predict capability for optimum operation of complex systems to prevent catastrophic events.

THE INVENTION

Summary of the Invention

The Totally Integrated Intelligent Dynamic Systems Display is an apparatus for graphically displaying analytical data, comprising a generic model to graphically represent a complex set of physical characteristics potentially leading to catastrophic failure of a physical system. The model comprises a depiction of wedge shaped regions extending outward from a central region, each of which is distinguished from others by color or pattern or other distinguishing feature. The wedge shaped regions represent predetermined subsystems of the physical system.

A series of concentric ridges overlap the wedge shaped regions and are substantially centered about the central region. Distance of each ridge from the central region represents functioning level as to the subsystems represented by the wedge shaped regions intersecting the ridge, and greater distance of ridges from the central region indicates greater respective functioning levels.

An icon is displayed depicting by color code an overall functioning level of the physical system is selected from the group consisting of: 1) an orb pulsating within the central region; 2) a rotating radar sweep extending from the central region, the sweep having an outer radius, said radius representative of a lowest failure bar for a subsystem with a lowest overall status level, said sweep rotating in a counter-clockwise direction when a most recent change in an overall status level is a decrease and rotating in a clock-wise direction at all other times; or 3) a ball rotating in an orbit defined by two ridges, the proximity of the ball's orbit to the central region being representative of an overall status level for the physical system, said ball rotating in a counter-clockwise direction when a most recent change in an overall status level is a decrease and rotating in a clock-wise direction at all other times.

The apparatus further comprises markers graphically depicting the functioning level of a subsystem by highlighting one or more of the ridges for a wedge shaped region, and one or more mappings, each mapping correlating predetermined characteristics of the physical system with the following in the generic model: functioning level represented by the ridges, subsystems of the physical system represented by the wedge shaped regions, overall functioning of the physical system and/or analysis of the physical characteristics represented in the icon. A sensor interface receives data including measurements of the physical characteristics of the physical system. A graphics generator prepares and displays a presentation of the generic model according to the measurements of the physical characteristics as correlated to the generic model by a selected one of the mappings.

BRIEF DESCRIPTION OF THE DRAWINGS

The invention is described in more detail with reference to the attached drawings, in which:

FIGS. 9A and 9B are, collectively, an exemplary Calculated Function Worksheet for the human renal subsystem, according to the invention;

DETAILED DESCRIPTION

The following detailed description illustrates the invention by way of example, not by way of limitation of the scope, equivalents or principles of the invention. This description describes several embodiments, adaptations, variations, alternatives and uses of the invention.

In this regard, the invention is illustrated in the several figures, and is of sufficient complexity that the many parts, interrelationships, and sub-combinations thereof cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

A. Generic Dynamic Error Model

1. Gravitational Well Format

Figure 1A:
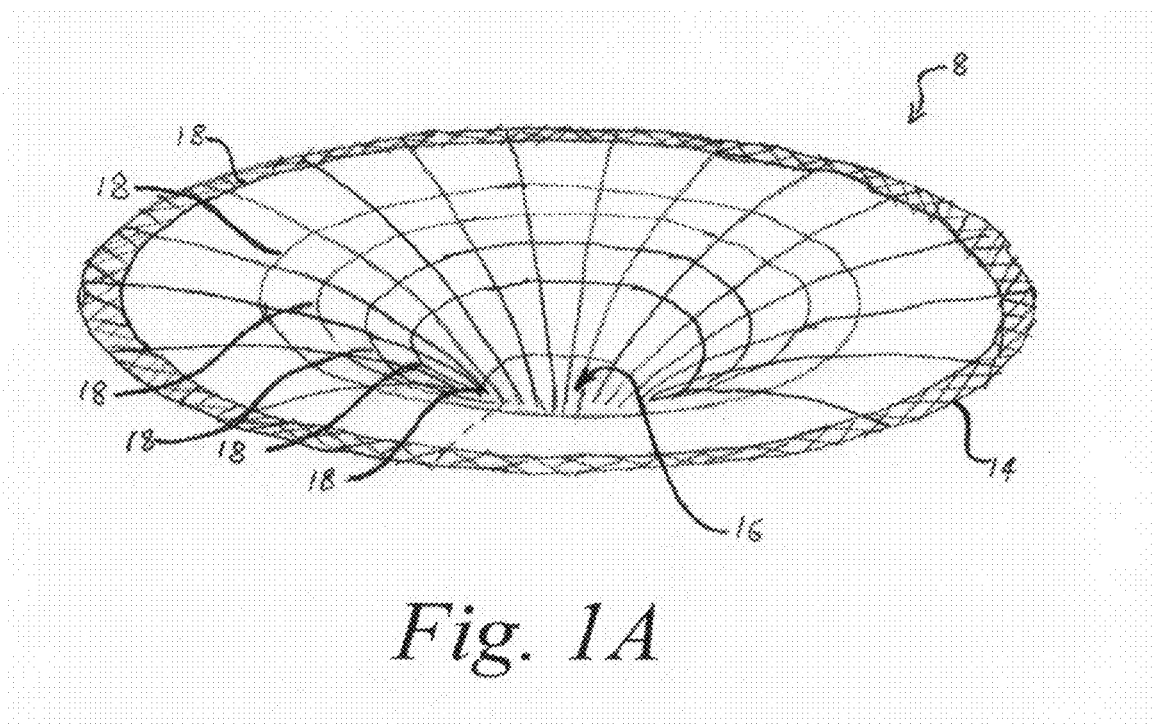
FIG. 1A is a photographic diagram of a perspective view of a gravity well, according to the invention.
Figure 1B:
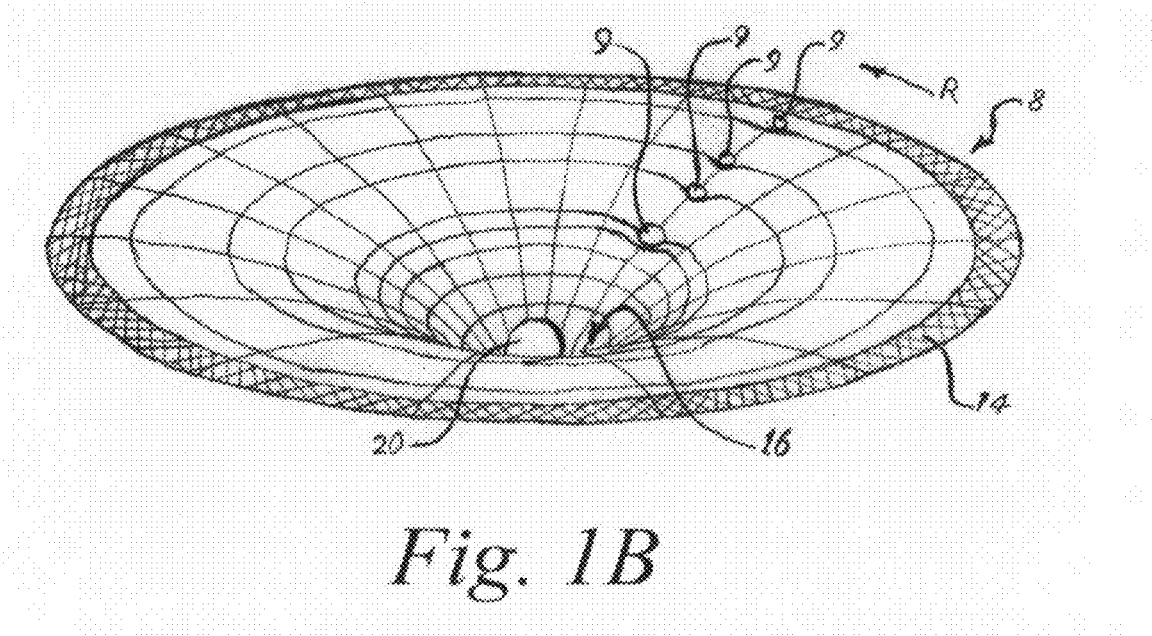
FIG. 1B is a photographic diagram of a perspective view of a gravity well with 4 balls rotating at different radiuses and one ball at the center of the well, according to the invention.

Referring to FIGS. 1A and 1B, the basic format for the dynamic error model is shown in three dimensions shaped as a gravitational well 8. Under Einstein's theory of general relativity, gravitational wells exist around the sun, around planets, and are created (in their extreme form) by black holes. Einstein theorized that gravity is a distortion of space with space akin to a thin rubber sheet. A heavy object, such as a billiard ball, placed on the sheet makes a dent. The force of gravity causes objects to behave in the well as if they are traveling inside a huge sink. A critical speed—the "orbital" speed—is needed to keep from falling to the bottom of the well.

FIG. 1A shows an example of the underlying physical form of the generic model of the present invention shaped as a gravitational well 8. The well 8 has an outer opaque ring 14, a central region 16, and concentric rings 18 of decreasing circumference between the outer ring 14 and central region 16.

FIG. 1B shows a similar gravitational well 8 with four balls 9 rotating counter-clockwise (as indicated by the arrow marked "R") within the gravitational well's 8 event horizon. The balls 9 are akin to planets orbiting the central region 16. The size of the four balls 9 increases as the balls 9 approach the central region 16 to graphically display an increase in the speed of rotation and a corresponding deteriorating situation. The balls 9 reverse rotation to clockwise in a steady state or improving situation. As discussed in connection with FIG. 2B, described below, the position of the balls and/or colors of the balls correspond to an assigned level of function of the system, with the position furthest away from the central region 16 indicating the highest/best level of function, and a position closest to the central region 16 indicating a severe condition.

Referring to FIG. 1B, an enlarged ball 20 is shown inside the central region 16. The enlarged ball 20 represents a catastrophic event for the system being monitored from which there is no recovery. One or more errors in the management of the system has caused the ball 20 to reach the center 16 of the gravitational well 8, and the situation has become catastrophic.

2. Gravitational Well with Added Features

The present invention utilizes the underlying shape and physical characteristics of a gravitational well with added visual features to represent various aspects of a complex system operating within the event horizon of the well.

a) Ridges

Figure 2A:
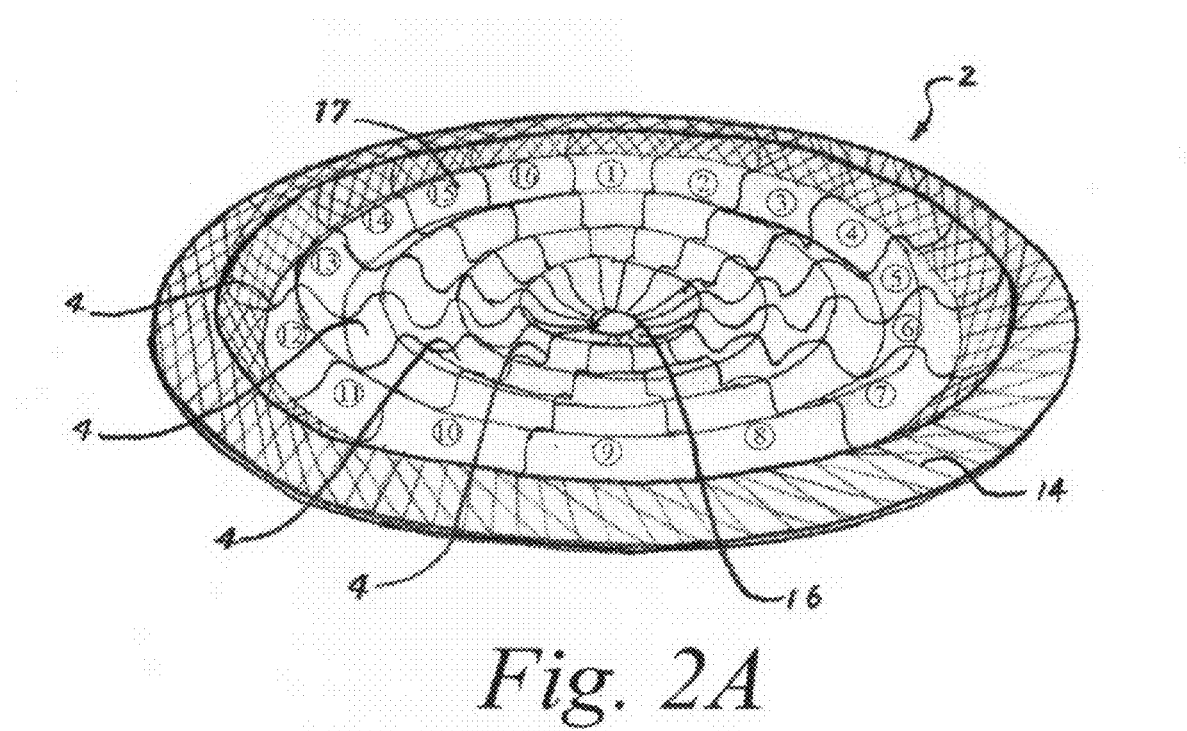
FIG. 2A is a photographic diagram of a perspective view of a gravity well with concentric ridges and wedges radiating from the center of the well, according to the invention.
Figure 2B:
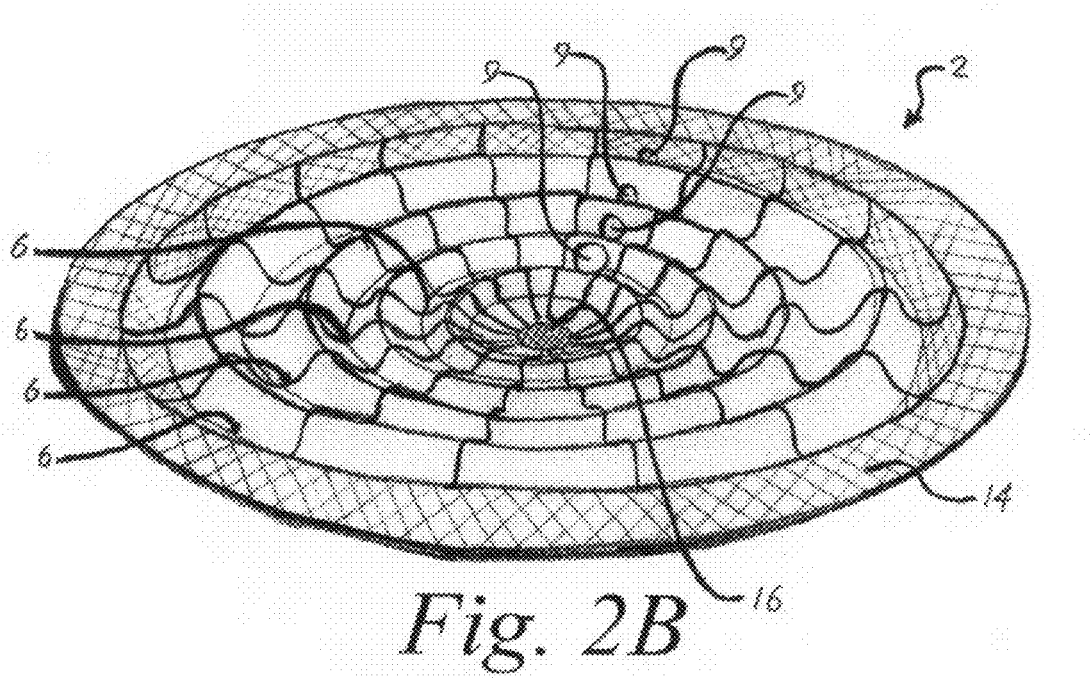
FIG. 2B is a photographic diagram of a perspective view of a gravity well with concentric ridges, wedges, and four rotating balls, according to the invention.

FIGS. 2A and 2B show examples of the generic model 2 with its most basic features. Referring to FIG. 2A, the model 2 comprises a series of five concentric, non-overlapping ring-shaped ridges or barriers 4 of decreasing circumference substantially centered about the central region 16. The ridges 4 are hill-shaped in cross-section. The perspective view of the model 2 is akin to a gravitational well with ripples in what would otherwise represent space in the well's event horizon. The ridges 4 represent a range of parameters or status levels for system performance.

Within each ridge 4, the range of status levels is distributed approximately evenly (i.e., linearly) between the ridge's inner and outer radii. There may be gaps between each ridge that provide visual separation, but are not used to indicate any status level. In the preferred embodiment, the inner and outer radii for each ridge correspond to the following percentage function levels: 80-100% (outer/first ridge); 60-80% (second ridge); 40-60% (third ridge); 20-40% (fourth ridge); 0-20% (central region). It should be understood that any suitable or desired number, shape or height of ridges may be utilized, and any suitable or desired range of status levels may be assigned to a particular ridge.

b) Wedges

Referring to FIG. 2A, the model 2 further includes color coded regions 7 on the ridges 4 representing different subsystems of the system being monitored. In the preferred embodiment, the color coded regions comprise differing colored pie-slice shaped wedges 7 radiating from the central region 16 outwards towards the furthest ridge. Each subsystem is assigned a color code with a key on the display explaining what each color represents. The parameters for the color-coded sections of each ridge are unique to that subsystem. In the preferred embodiment, the number of subsystems is represented with equally-sized wedges, non-overlapping, which together form a full circle. In the preferred embodiment, within each pie-slice wedge, the ridges are colored or patterned to correspond to a particular subsystem, except the outer ring which remains a uniform color. Any suitable or desired number or width of wedges, or design utilizing a variation in the shape and appearance of different wedges, may be utilized.

In the preferred embodiment, the four most important subsystems (i.e., the key subsystems to avoiding disaster/death in the system being monitored) are positioned vertically and horizontally to form a Maltese cross.

c) Pulsating Orb or Radar Sweep

Figure 7:
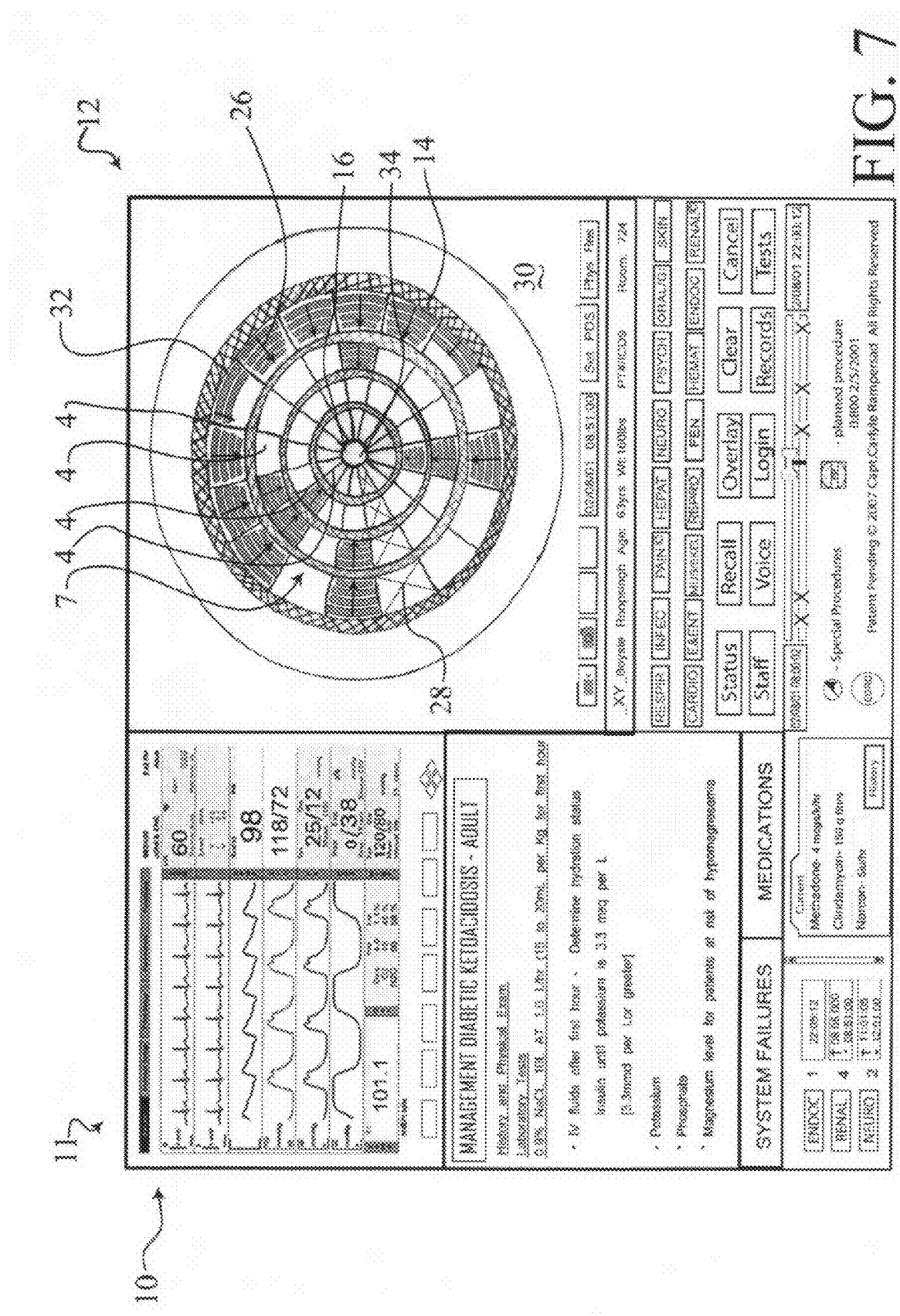
FIG. 7 is a photographic diagram of an exemplary screen display with TIIPS model, according to the invention.
Figure 8:
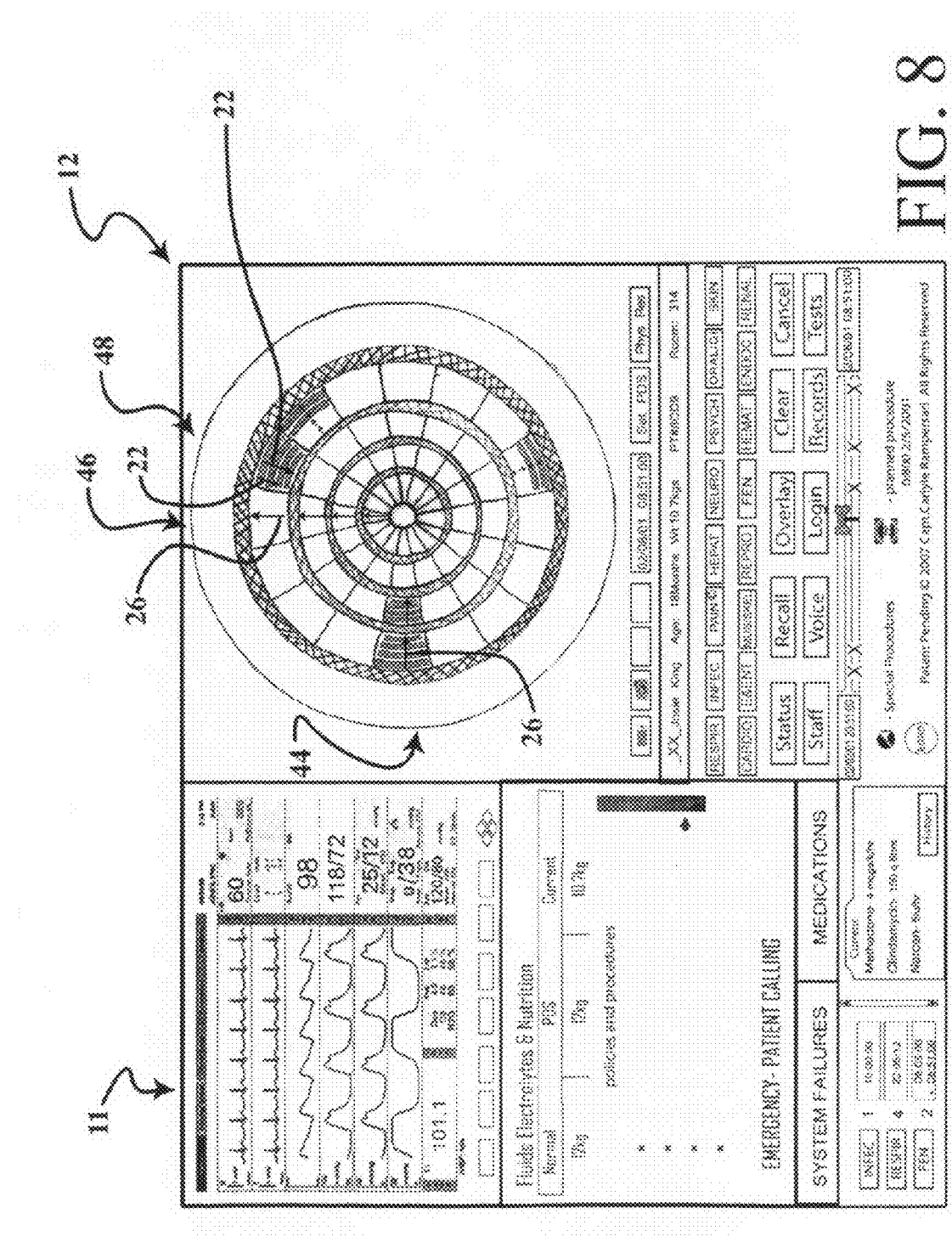
FIG. 8 is a photographic diagram of an exemplary screen display with TIIPS model, according to the invention.

Referring to FIGS. 7 and 8, in the preferred embodiment, an icon comprising a colored orb 34 is shown pulsating within the central region. The color of the orb 34 represents the Overall Status Level ("OSL") of the system. The OSL comprises the minimum of current status levels of all subsystems for which there is data. Any systems for which the system has no information are not included in this calculation. The following colors are assigned the following OSL's: red for an OSL below 20%; amber for an OSL below 40% but not below 20%; yellow for an OSL below 60% but not below 40%; green for an OSL not below 60%. The orb 34 pulses at a rate that is not distracting to the eye but suggests that the system is working, such as a rate of approximately four pulses every five seconds. The pulse rate may be made dependent on the OSL.

Other types of stationary and/or orbiting icons may be utilized to indicate the OSL of the system being monitored, including, without limitation, a radar sweep, a rotating ball, flashing icons, and/or stationary or moving icons of differing shapes. In the case of a radar sweep, the icon is displayed as a rotating, colored sweep image extending from the central region, reminiscent of a radar display. The sweep rotates counter-clockwise when the most recent change in the OSL is a decrease, and clockwise at all other times. The sweep color is dependent on the current OSL, using the same algorithm as for the pulsating orb's color. The sweep's reach (outer radius) also is dependent on the current OSL. The sweep reaches to approximately the same radius as is indicated by the inner edge of the lowest failure bar 32 for the subsystem with the lowest current OSL (i.e., the subsystem that is currently determining the OSL). Failure bars 32 are further discussed below in connection with FIGS. 7 and 8. The preferred sweep rate is approximately 15 revolutions per minute. The sweep rate may be made dependent on the OSL. The operator of the system may turn the sweep on or off, as desired and/or may choose a different icon such as the pulsating orb. Sounds or alarms also may be utilized to alert persons managing the system to a change in condition.

An alternate embodiment displays the icon as a ball rotating within an orbit defined by the ridges 4. Referring to FIG. 2B, four balls 9, akin to planets, are shown orbiting a gravitational well. The orbits are in valleys 6 defined by the ring-shaped ridges 4. Although four balls are shown in FIG. 2B in four different orbits for purposes of demonstrating the different orbits possible, in operation of this alternate embodiment, only one ball 9 is displayed at a time orbiting in one valley 6. The ball's 9 movement as it orbits the central region 16 represents the passage of time. The location, speed and color of the ball 9 provide the viewer of the display with instant information regarding the overall status of the system being monitored. In general, the further the ball 9 orbits from the central region 16, the better the system is functioning. Likewise, as the ball 9 breaches one or more ridges 4 and orbits closer in proximity to the central region 16, the position of the ball 9 represents a deteriorating condition of the system. As the ball 9 approaches the central region 16, its orbit increases in speed in correlation to the smaller circumference of the inner ridge(s) 4. The ball 9 changes color as it approaches the central region 16, e.g., from green, to yellow, to amber, to red, as conditions worsen. The ball 9 also changes direction when conditions change. The ball rotates counter-clockwise when the most recent change in the OSL is a decrease, and clockwise at all other times.

Figure 3A:
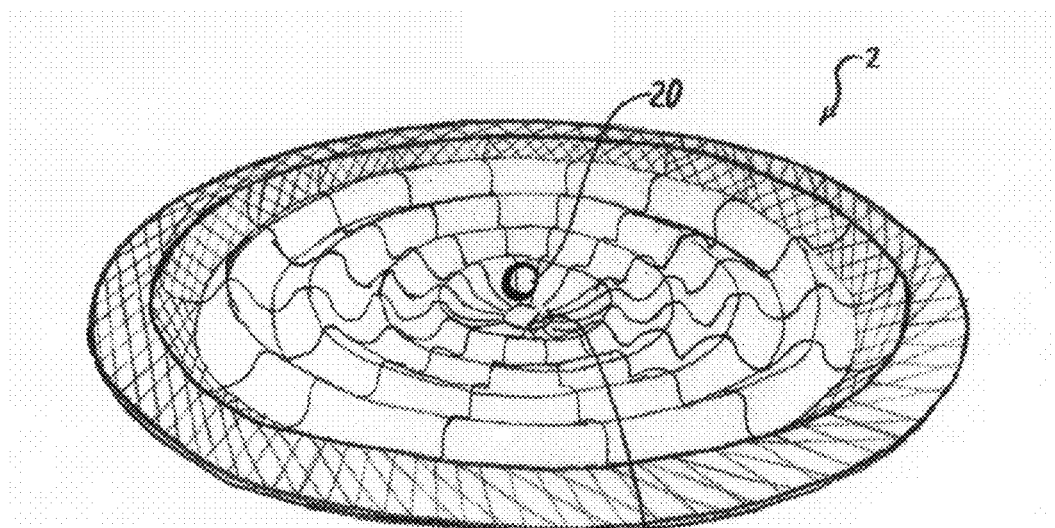
FIG. 3A is a photographic diagram of a perspective view of a gravity well with concentric ridges, wedges, and a ball at the center of the well, according to the invention.

FIG. 3A shows a three-dimensional perspective view of the generic model 2 upon a rotating ball icon reaching the central region 16 graphically representing a catastrophic event 20.

d) Status Arrows

The generic model 2 comprises a manner in which changes in subsystem performance are represented and displayed to a viewer. In the preferred embodiment, changes in subsystem performance are indicated by status arrows 26 as shown in FIG. 7. For each subsystem with a status level below 90%, the apparatus is programmed to draw arrows 26 within that subsystem's wedge segment 7 that point inward towards the central region 16. The arrows 26 start from the radius corresponding to a status level of 90%, and end at the radius corresponding to the current status level for that subsystem. The arrows 26 are drawn so that an arrow shaft never crosses the gap between barrier ridges. Wherever an arrow shaft reaches the inner edge of a ridge 4, an arrow head is drawn. Arrow heads are also drawn at other points along the arrows' shafts in order to visually reinforce the arrow's 26 direction.

Likewise, for any subsystem 7 whose current status level is greater than its minimum recorded status level, the apparatus draws arrows 26 that point outward from the central region 16, up to a maximum of 90%, within that subsystem's wedge segment 7. The arrows 26 start from the radius corresponding to the minimum recorded status level, and end at the radius corresponding to the current status level.

e) Failure Bars

The generic model 2 comprises a manner in which failures in a subsystem are represented and displayed to a viewer. In the preferred embodiment, as shown in Quadrant B of FIGS. 7 and 8, changes below 80% in functioning are represented by arc shaped failure bars 32 drawn at intervals of five points from the radius corresponding to a status level of 80% down to the radius corresponding to the current status level.

f) View Options

Figure 10A:
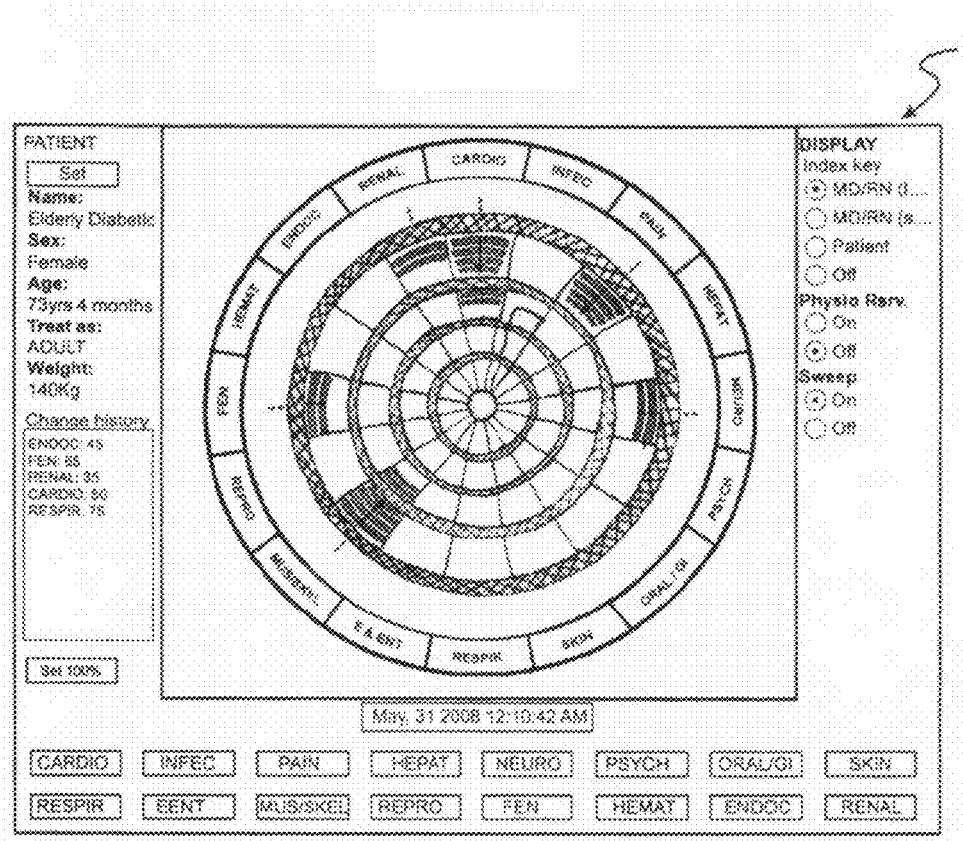
FIGS. 10A and 10B are photographic diagrams of exemplary TIIPS screen displays for a young, healthy traumatic accident scenario, according to the invention.
Figure 10B:
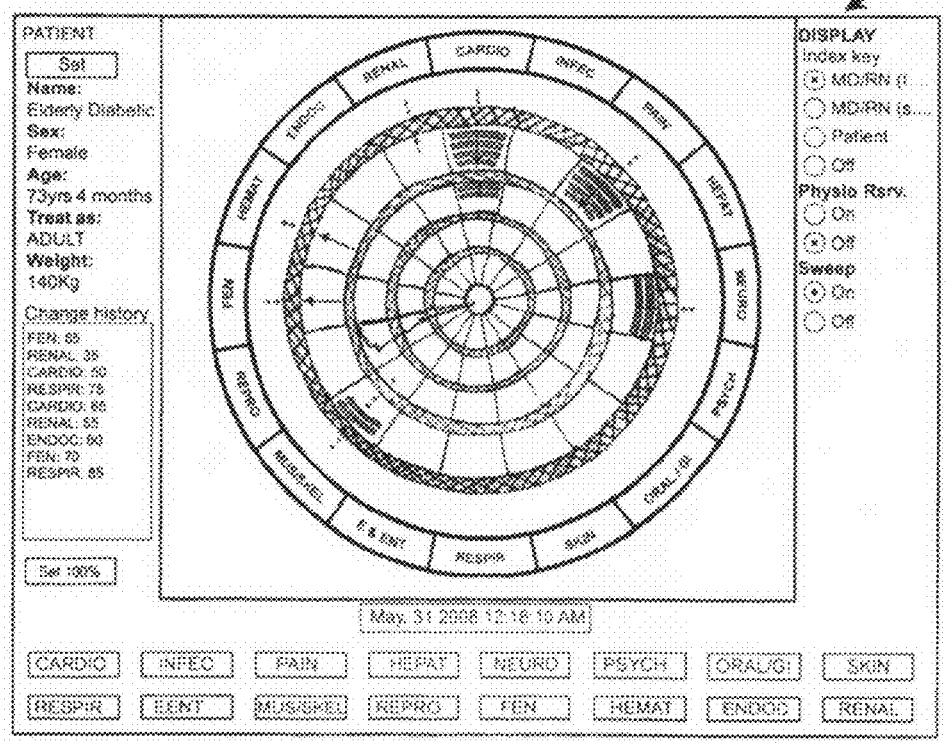

The model 2 may be shown in three dimensions as illustrated by FIGS. 2A and 2B, two dimensions as illustrated by FIGS. 7, 8, 12 and 13, or in a sectional view with wedges separated in a line or grid as partially shown in FIGS. 10A and 10B. The apparatus may be programmed to present the model in various modes, giving the viewer the option to select a preferred view. The display may be generated on any electronic screen display, including, but not limited to, personal computers, laptop computers, notebook computers, tablet computers, personal digital assistants ("PDAs"), cellular phones, and smart phones. Alternately, the display may be projected onto a flat surface for viewing.

The graphics generator may include a graphics interface (as shown in FIGS. 7 and 8) to provide a viewer a manner in which to interact with the display.

Figure 3B:
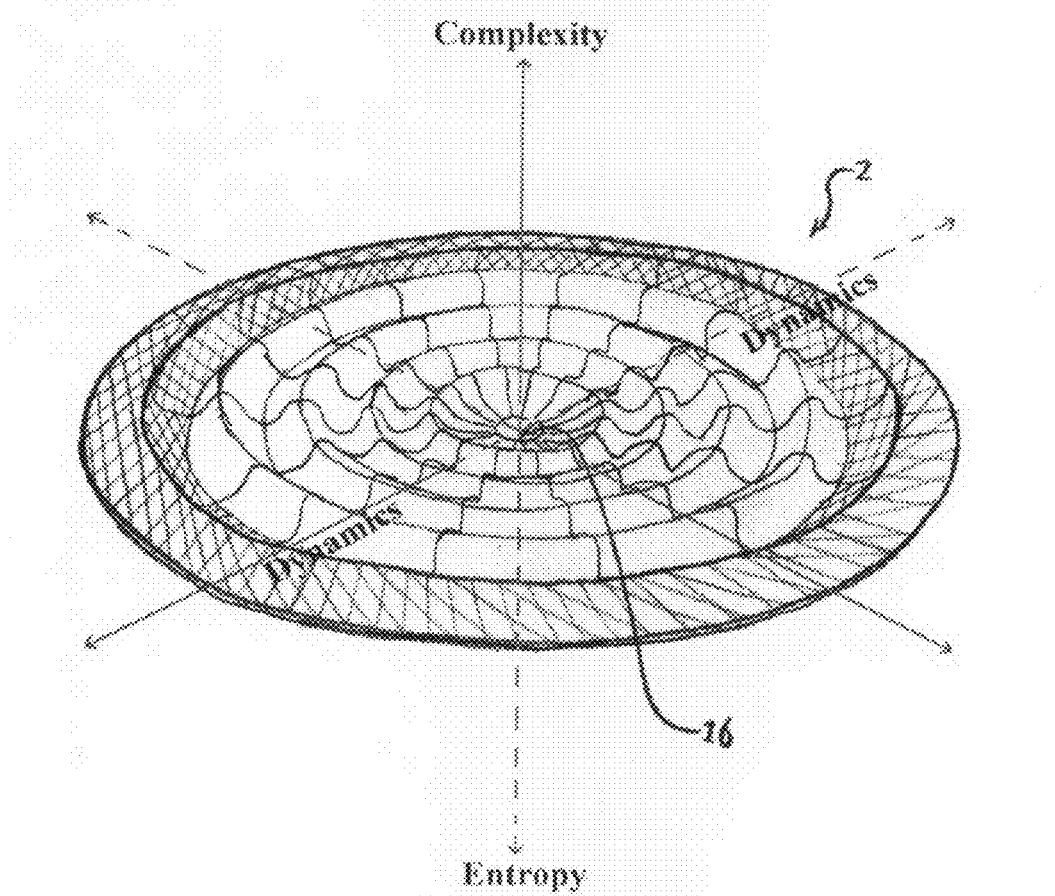
FIG. 3B is a photographic diagram of a perspective view of a gravity well with concentric ridges, wedges and arrows indicating dimensions and direction of increasing complexity and dynamics of the system, according to the invention.

FIG. 3B shows a three-dimensional view of the model 2 with arrows along labeled vertical and horizontal axes. The vertically oriented axis arrow is labeled "complexity" at its top end, and "entropy" at its base end. Complexity increases with the height of the model 2, and entropy increases towards the base of the model and below, with the central region 16 corresponding to a catastrophic event from which there is no recovery. The horizontally oriented arrow is labeled "dynamics" and represents changes over time. Rotation along the dynamic axis indicates the passage of time.

3. Generic Model System Configuration

Figure 4:
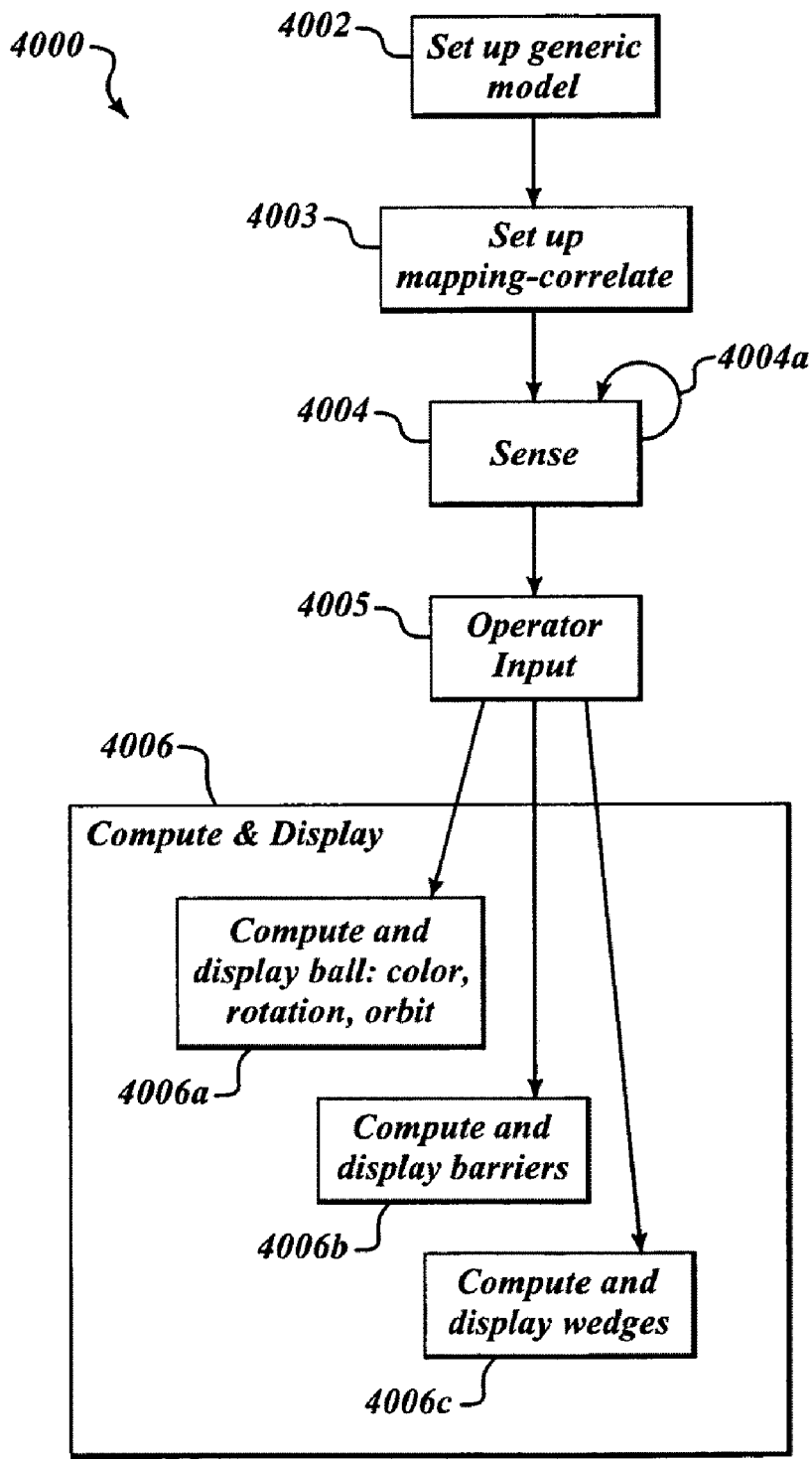
FIG. 4 is a block diagram of the configuration of the apparatus based on the generic model, according to the invention.

FIG. 4 is a block diagram of the system configuration for an exemplary TIIDS apparatus 4000 according to the invention. A generic model 4002 is programmed or downloaded to one or more computers. Mapping correlates 4004 are programmed or downloaded to one or more computers. The mapping correlates 4004 comprise parameters for specific subsystems, ridge or barrier levels within subsystems, and parameters for the position, color and direction of a stationary or rotating icon. The sensor interface 4005 comprises a first set of sensors to receive and analyze situational data 4005A, and a second set of sensors to receive and analyze operator input data 2005 from at least one user interface.

Referring to FIG. 4, the apparatus 4000 includes a graphics generator application program 4006 resident in at least one computer to generate and display at least one TIIDS display 4006 on at least one electronic screen display, said display comprising an icon 4006A, barriers 4006B and subsystem wedges 4006C. The program comprises the functionality of: access to the generic model 4002; access to one or more mapping correlates 4004; access to data supplied by at least one sensor interface 4005, and automatic generation and display of at least one TIIDS display 4006.

B. Medical Application

The invention as applied to the medical field is referred to as a Totally Integrated Interactive Patient Systems Display ("TIIPS" or "TIIPS display") wherein the physical system graphically represented is at least one human body. TIIPS is an apparatus providing a three-dimensional real time dynamic error model visually displaying the status of the multiple subsystems within a human patient. The data regarding the various sub-systems of the patient are integrated into a visual display based on the generic model 2. The physician and other care takers of the patient may then interact with the TIIPS model. The system is further designed to be improved over time through: 1) physician or hospital updates (e.g., setting new protocols); 2) the integration of updated information available over the internet, such as ethnic and geographically relevant data; and 3) statistical analysis of the data collected by the system over time to set new and better parameters.

Overall, the system allows various members of a patient's care team to share information in real-time to improve patient care and prevent catastrophic errors that would otherwise lead to the patient's death. The medical application herein disclosed may be used to monitor the life status and care of any living being, human or animal, and is not limited to the hospital setting.

1. Generic Model Applied to the Human Life System

Figure 5:
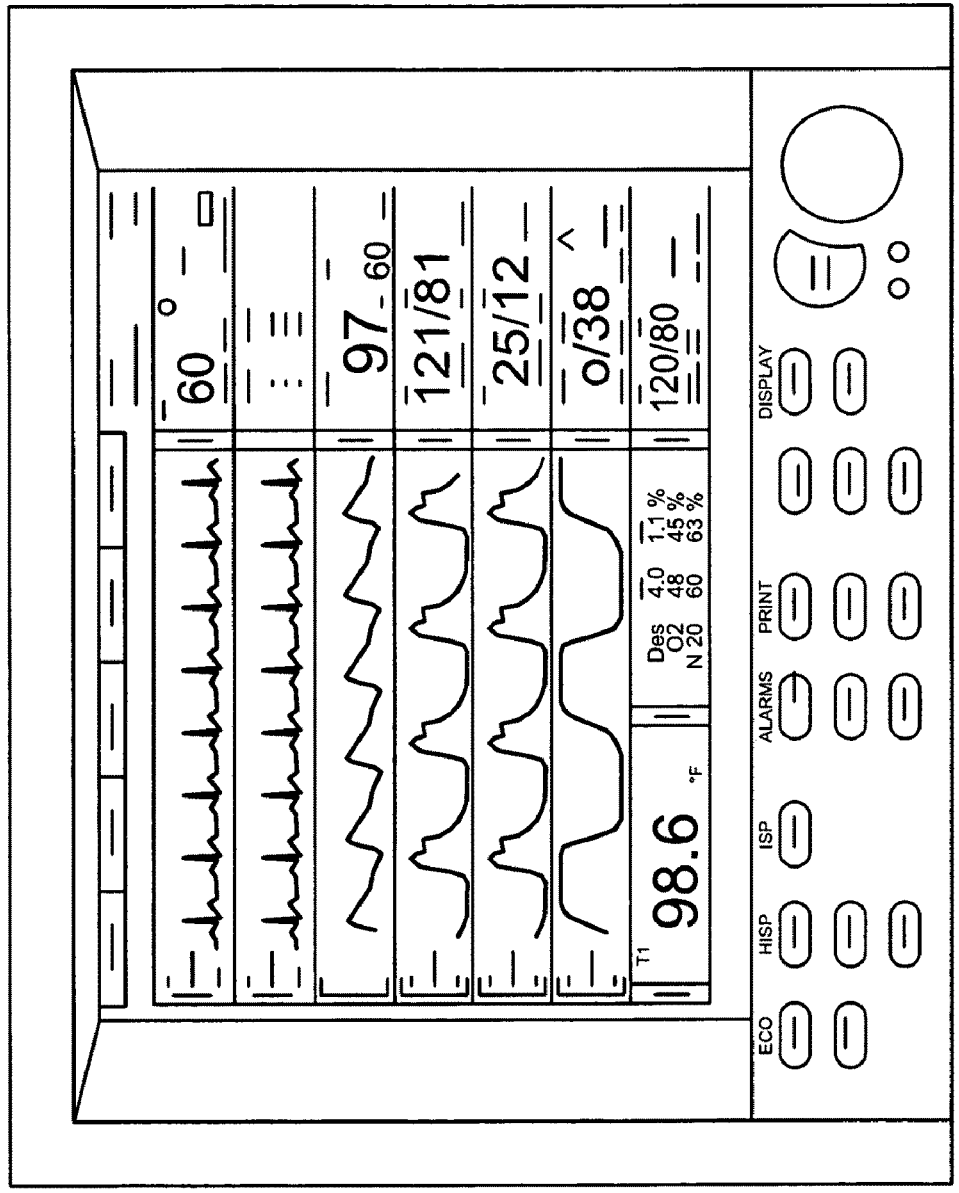
FIG. 5 is a diagram of a typical, prior art screen display used in hospitals for the monitoring of critical care patients.

FIG. 5 shows an exemplary, prior art screen display 10 typically used in hospitals for the monitoring of critical care patients. As shown in FIG. 5, various systems of the patient's well-being are actively monitored. However, the information is provided in separate categories and assigned numerical values relying on the care-taker to assess the condition of the patient. The monitor 10 also does not provide the care-taker with information regarding the patient's history of treatment or other unique characteristics that may impact treatment decisions and their outcome.

As discussed in connection with FIG. 11, described below, the TIIPS apparatus takes the information as previously displayed in a fashion as shown in FIG. 5, and converts that data to the generic model 2 format, discussed in connection with FIGS. 1A-4, described above. Specifically, the living human system as a whole is represented by: 1) a gravitational well having a central region representing failure of the physical system (death); 2) a series of concentric ridges substantially centered about the central region, where proximity of the ridges to the central region is representative of criticality of one or more subsystems to avoiding death; 3) wedge shaped regions upon the ridges extending outward from the central region representing various subsystems of the human being, with each wedge being distinguished from the others by color or pattern or other distinguishing feature; and, 4) an icon representing the passage of time, where the color, position, shape and/or rotation of the icon represents prescribed analysis of the physical status of the human patient being monitored.

The computer operating the system is pre-programmed with mappings correlating to predetermined characteristics for each of the ridges and subsystems. In the preferred embodiment, the first (most outer) ridge represents functioning at an 80 to 100% level; the second ridge represents functioning at a 60 to 80% level; the third ridge represents functioning at a 40 to 60% level, and the fourth ridge represents functioning at the 20 to 40% level. For each patient, the system keeps a status record of each individual body system belonging to that patient. Any body system may have a status level of 0% to 100%. Zero indicates a complete failure of that system, while 100% indicates 100% normal function. For each body system, the system also stores the minimum status level and the previous status level, that is, the status level prior to the last update.

Each subsystem is assigned a range of characteristics corresponding to each percentage range (20 to 40, 40 to 60 and so on). In the preferred embodiment, multiple "mapping" criteria are used to assign a Percentage Functioning Level for each subsystem, discussed in connection with FIGS. 9A-9F, described below.

2. Generation of a Display Integrating TIIPS Model with Additional Data

Figure 6:
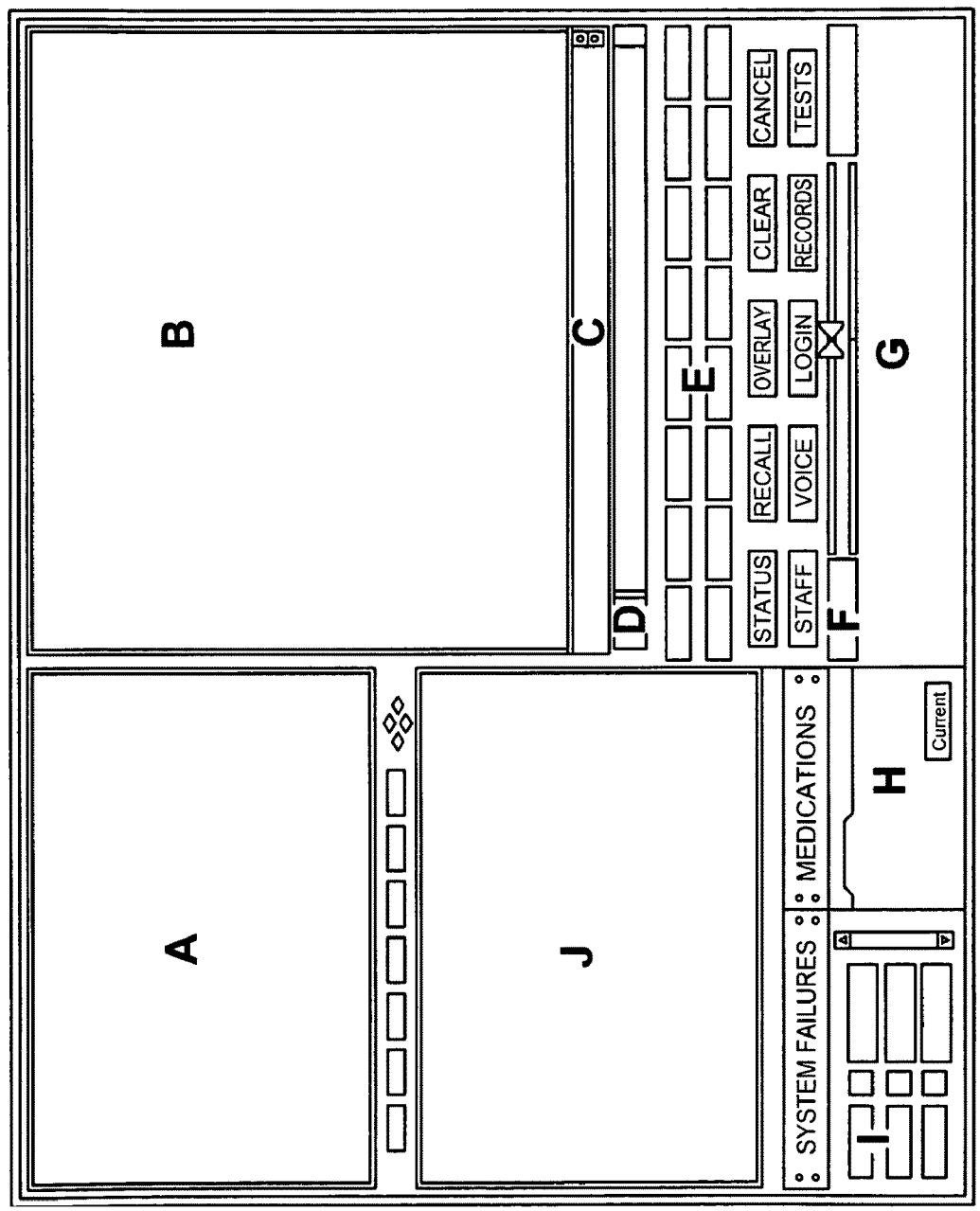
FIG. 6 is a diagram of exemplary quadrants on a computer screen display, according to the invention.

FIGS. 7 and 8 are diagrams of exemplary TIIPS displays for monitoring the condition of human patients. In a hospital setting, the TIIPS model may be integrated with additional data on a screen display 11 to assist in patient care and monitoring. FIG. 6 shows exemplary quadrants on a computer screen display with exemplary corresponding data and visual graphics shown in FIGS. 7 and 8. The screen displays 11 of FIGS. 7 and 8 are exemplary, only. Various rearrangements and variations in displayed data may be utilized. The icons on the display 11 may be programmed to activate in response to a computer mouse, touch, voice command, trackball, joystick, dials, and any one or combination of user interfaces suitable for the purposes of this disclosure.

a) Prior Art Display and TIIPS Model Display

Referring to FIGS. 6 and 7, Quadrant A at the top left hand corner of the screen display 11 shows the patient information 10 in a format as currently displayed in the prior art. This provides continuity for hospital personnel between use of the prior system and the TIIPS model. Over time, the prior art display 10 may be eliminated if no longer necessary. In an alternate embodiment, Quadrant A contains thumbnail views of TIIPS models 12 for multiple patients being monitored, such as at a nursing station. Upon selection of one of the thumbnails for a particular patient, that patient's individual information is displayed in an enlarged view in Quadrant A or one of the other quadrants of the display 11.

Referring to FIGS. 6 and 7, Quadrant B displays, in top plan view, the TIIPS model 12 comprising concentric ridges 4 and color-coded wedge-shaped subsystems 7 (only one subsystem is called out in FIG. 7, however there are 16 wedges shown).

The computer generating the TIIPS model 12 shown in Quadrant B is programmed to display a pulsating orb 34 at the central region 16, however, any suitable or desired icon or set of icons may be programmed for graphic display of the passage of time and/or current condition of the patient based on the TIIPS model 12.

In an alternate embodiment, the icon comprises a radar sweep. The radar sweep emanates from the central region 16 and the computer is programmed to signal the condition level of the patient by the sweep's color, direction of rotation, and/or length. For example, a green colored radar sweep flowing in a clockwise direction and extending from the central region 16 to the outer ridge 4 indicates a stable (homeostatic) or improving condition. On the other hand, an amber-colored radar sweep moving in a counterclockwise direction and extending to only the second ridge 4 from the central region 16 would indicate an unstable or deteriorating condition. The direction, color, and/or length of the sweep indicate the last change (i.e., most recent change) in the patient's status, and the most critical subsystem governs based on a hierarchy of the subsystems programmed into the computer displaying the model.

Referring to Quadrant B of FIG. 7, the application is further programmed to display status arrows 26 within each ridge 4 to visually indicate the status level of a particular subsystem 7. An arrow 26 pointed inward towards the central region 16 indicates a deteriorating trend in a subsystem 7; an arrow 26 pointed outward indicates an improvement.

Referring to Quadrant B of FIG. 7, the computer may further be programmed to display failure bars 32 within each ridge 4 for a particular subsystem 7. The failure bars 32 shown in FIG. 7 represent an 80% or below percentage functioning level for that particular subsystem 7 within the parameters established for the ridge 4 level. For example, if the data entered indicates that a patient's renal system is functioning at a 75% optimum level within the parameters set for the outer ridge 4 for that subsystem, the computer is programmed to generate and display the subsystem 7 with a shaded failure bar 32 and arrow 26 pointing toward the central region.

As previously disclosed, each ridge 4 represents a range of 20% of functioning level for the patient (the first ridge represents 80 to 100% functioning level, the second ridge represents 60 to 80% functioning level, and so on). Referring to the TIIPS model 12 of FIG. 7, the failure bars 32 within each ridge 4 represent intervals of 5% of functioning level below 80%. Thus, there are a maximum of four failure bars 32 in each ridge 4, representing intervals of 5% functioning. In the outer ridge 4, the failure bars 32 represent functioning levels of 95%, 90%, 85% and 80%. In the second ridge, the failure bars 32 represent functioning levels of 75%, 70%, 65% and 60%. The failure bars 32 provide a visual representation of the percentage level of function for a particular subsystem 7.

The apparatus generating the TIIPS model 12 shown in Quadrant B of FIG. 7 is further programmed to display each of the major subsystems 7 in the human body with an assigned color code. For exemplary purposes, Quadrant B shows 16 major subsystems 7. The subsystems 7 may be of any preferred number, may be displayed in any preferred order within the model 12, and may be distinguished by color, pattern, or any other distinguishing feature. For exemplary purposes, only, the wedge shaped regions 7 on the TIIPS model 12 shown in FIG. 7 total 16 and are color coded as follows:

1. Respiratory (Lungs)—coded blue
2. Cardiovascular (Heart and Blood vessels)—coded red
3. Neurological (Brain and Nerves)—coded gray
4. Renal (Kidneys)—coded yellow
5. Hepatic (Liver)—coded green
6. Hematological (Blood Components)—coded crimson
7. F.E.N. (Fluids, Electrolytes and Nutrition)—coded light crimson
8. Infection—coded light gray
9. Oral/GI (Gastro-Intestinal)—coded brown
10. Muscular-Skeletal—coded off-white
11. Pain—coded dark purple
12. Eyes & ENT (Ear, Nose and Throat)—coded cream
13. Reproductive—coded light blue
14. Skin—coded tan
15. Endocrine—coded teal
16. Psychological—coded light purple Referring to Quadrant B of FIG. 7, the computer may further be programmed to display a series of X's 28 on any subsystem 7 for which the computer has no data entered. In FIG. 7, the subsystem 7 for which there is no data entered is the "Reproductive" subsystem, and X's 28 are displayed on the wedge representing that subsystem.

The computer generating the TIIPS model 12 may be further programmed to display a background 30 of a particular color, pattern, flashing pattern, or combination thereof to signal to the viewer additional indications as to the patient's status.

b) Patient Disease Specific Values and Physical Reserve

Referring to Quadrant C of FIG. 7, the screen display comprises dual icons labeled "Set PDS" and "Phys Res". "Set PDS" stands for "Set Patient & Disease Specific Values" and is an icon that upon activation, provides electronic means for a physician to set certain parameters for the patient that will be reflected within the TIIPS model, discussed in connection with FIGS. 9A-9F, described below. "Phys Res" stands for "Physical Reserve" and is an icon that upon activation, provides electronic means for a physician to enter data regarding the capacity of the patient to bounce back from medical procedures.

c) Patient Statistics

Referring to Quadrant D of FIG. 7, the computer is programmed to display basic data regarding the patient, including the patient's genotypic data represented by chromosomal indicia, the patient's name, age, weight, diagnosis, and room number. The computer is programmed to take the patient's age and weight into consideration when setting the mappings for the system. The system is further programmed to calculate an overall status level ("OSL") for the patient, comprising the minimum of current status levels of all monitored body systems for that patient. Any body systems for which the system has no information are not included in this calculation. The OSL is reflected in the color of the pulsating orb at the central region, and in the preferred embodiment, is coded red for an overall status level below 20%; amber for an overall status level below 40% but not below 20%; yellow for an overall status level below 60% but not below 40%; and, green for an overall status level not below 60%.

d) Subsystem Icons

Referring to Quadrant E of FIG. 7, the computer is programmed to display color coded icons for each subsystem 7 represented graphically in the TIIPS model 12 of Quadrant B. Upon activation of a subsystem icon, the computer is programmed to display textual information in Quadrant J regarding the status of that subsystem. The application may be further programmed to display ACLS and other protocols related to that subsystem. The textual data displayed is not limited to simple organ information, but extends as broadly as possible to all aspects of the subsystem involved. In FIG. 7, the "Renal" subsystem icon has been selected, with corresponding textual medical information shown displayed in Quadrant J. The "C" in a circle on the "Renal" icon indicates there has been a consult requested for that subsystem for the patient. By activating the icon and having the computer generate the textual information in Quadrant J, a viewer of the display is able to determine whether the consult has been completed, and if so, the updated data resulting from that consult.

e) Display Icons

Referring to Quadrant E of FIG. 7, the computer is programmed to display multiple icons relating to management of the display 11. The "STATUS" icon, when activated, causes the program to display the most current view available. The "RECALL" icon, when activated, causes the program to display the previous view. The "OVERLAY" icon, when activated, causes the program to display the TIIPS model compressed over a period of time as selected from the scroll bar in Quadrant F. The "CLEAR" icon, when activated, causes the program to clear the screen. The "CANCEL" icon, when activated, causes the program to prompt the viewer with a choice of features to cancel, such as an alarm sound. The "STAFF" icon, when activated, causes the program to display the current hospital staff assigned to the patient along with contact information. Alternate embodiments include means for automatic communication to a staff member chosen by the viewer of the display, e.g., an automatic telephone call, e-mail, or other electronic signal to the chosen staff member. The "VOICE" icon, when activated, causes the program to respond to voice commands.

Referring to Quadrant E of FIG. 7, the "LOGIN" icon, when activated, causes the program to display a login screen for entry of a password or other access-specific information. The hospital may limit access to patient records and to entry of data about a particular patient that would change the TIIPS model to certain staff members. The application may be further programmed to generate and display different levels of information depending on the access code provided. For example, a physician would be given access to information regarding Patient & Disease Specific Values, discussed in connection with FIGS. 9A-9F, described below. On the other hand, a family member or patient advocate would be provided a different code to log into the system and access the patient's display for family level screening. In that event, the computer would provide access to less and/or simplified data.

Referring to Quadrant E of FIG. 7, the "RECORDS" icon, when activated, causes the program to display a screen whereby a physician selects particular patient records and sets a password for access to those records. The physician then communicates the password to a third party in need of reviewing those records, such as a specialist, and only upon entry of the correct password, would the specialist be given access to the selected records.

Referring to Quadrant E of FIG. 7, the "TESTS" icon, when activated, causes the program to display test results in Quadrant J. If a viewer desires to see test results for a particular time period, the viewer may select the time period using the slider in Quadrant F.

Referring to Quadrant F of FIG. 7, sliding bars are displayed for selection of a range of dates and times for data. Boxes with Xs are displayed to indicate significant events in the patient's history for the time period selected, such as anesthetics and surgery. By selecting a particular box and selecting the "RECALL" icon, the computer is programmed to display the historical TIIPS model and associated data for the patient at that previous point in time.

f) Procedure Icons

Referring to Quadrant G of FIG. 7, the display 11 includes an icon labeled "Special Procedures" which, upon activation, provides textual information in Quadrant J regarding current required procedures for the proper care of this patient. The icon labeled "Planned Procedure", upon activation, provides textual information in Quadrant J regarding upcoming procedures for the patient, including the nature of the procedure and the physician(s) assigned.

g) National Database Queries

Referring to Quadrant G of FIG. 7, the display 11 includes an icon labeled "EGRD" which stands for "Ethnic and Geographically Relevant Data." As further discussed herein, the TIIPS model may integrate data available over the internet from national research databases regarding new medical discoveries relating to genetic and/or geographic factors. A user of the system may query the national databases based on a genetic profile of the patient to determine whether there are significant risks for a particular procedure for the patient. Likewise, a user may query databases to determine whether a patient was in an area where there was an outbreak of a particular illness. In an alternate embodiment, the application is programmed to automatically mine the databases for data relevant to the particular patient and alert the viewer to the information for potential inclusion in the TIIPS model.

h) Medications

Referring to Quadrant H of FIG. 7, the display 11 includes a textual display of the current medications being administered to the patient as well as an icon for "History" which, when activated, provides historical information regarding medication, along with dates of use and any signs of contraindications. A portion or all of Quadrant H may be color coded to indicate which subsystem is being treated with a particular drug.

i) System Failures

Referring to Quadrant I of FIG. 7, the display 11 includes a representation of system failures in descending chronological order, the level of each failure (1 through 4, with 4 being the most severe, depending on the ridge level reached on the TIIPS model), and the time interval for the failure. Each system failure is represented visually on the TIIPS model 12 by a lowering of the function of that subsystem 7 to at least one ridge level 4 closer to the central region 16. Previous system failures may be viewed using the slider to scroll down the list. Selection of an icon for a particular system failure will result in textual details regarding that failure to be displayed in Quadrant J.

j) Textual Information

Referring to Quadrant J of FIG. 7, a portion of the display 11 is reserved for textual information, as previously disclosed. Quadrant J is utilized to display a variety of information and data, including display of the recommended protocols for the current condition of the patient. For example, in cardiac or respiratory failure, the computer may be programmed to display ACLS (Advanced Cardiac Life Support) protocols established by the American Heart Association.

3. Immediate Visual Assessment of Patient Condition

Referring to FIG. 8, a display 11 that includes the TIIPS model 12 gives the care-taker an immediate visual summary of the overall condition of the patient as well as trends in the patient's status. FIG. 8 is a screen display 11 that illustrates a sequence of fictional events in the care of an 18 month old infant. The data in the screen display 11 represents the care provided to the infant after she stepped into a hot bath and received non life threatening burns on her legs.

Referring to the TIIPS model 12 in FIG. 8, the pain she was experiencing due to the burns is illustrated as that subsystem 44 functioning at a 40% level (the arrows 26 are pointing inwards and extend down to the 40% radius level). After admission to the hospital, she suffered total collapse of her Respiratory System 46, was put on an artificial breathing apparatus (Ventilator) and made a full recovery. The initial collapse of her Respiratory System 46 would be illustrated by inward arrows 26 down to 0% functioning level. The full recovery is shown in FIG. 8 with arrows 26 in the Respiratory System 46 pointing outwards to indicate an improved condition.

However, after the recovery of the Respiratory System 46, the child developed a slight infection in her skin (illustrated as the skin subsystem 48 functioning at a 70% level with infection arrow 22). She subsequently developed a slight Bacteremia (bacterial infection in her blood), illustrated by a second infection arrow 22 down to the 60% functioning level. Despite the recovery of her Respiratory System, the display 11 provides on-going updates on her condition and continues to draw attention to the infections and related conditions, such as dehydration and pain, which will need to be monitored. The display 11 and TIIPS model 12 is programmed to provide warnings to the family and staff at each level of failure and cannot be ignored, for reasons including, required interaction to silence alarms.

4. Interaction with Apparatus a) Physician Generated Situational Data

Each application involving the TIIDS model 12 comprises mappings correlating to predetermined characteristics of the physical system being monitored. The mappings are pre-established and programmed for each subsystem. However, additional data must be provided to the system about the unique characteristics and/or current status of the system through a sensor interface. In the case of the medical application, as part of the sensor interface, the physician provides additional data, referred to herein as "situational data," unique to the patient which is then displayed as part of the TIIPS model.

1) Patient & Disease Specific Values

In the medical application, the situational data established by the physician for each patient includes Patient & Disease Specific Values ("PDS Values"). The physician decides the PDS Values for each affected subsystem in the patient. Factors that affect the PDS Values include a patient's age, weight, ethnic origin, environment, culture, habits, geographical location, genetic markers, smoking, level of recurrent activity, and physician bias, knowledge, and experience. The PDS Values are strictly physician-driven in the current preferred embodiment. Over time, PDS Values will become more fixed in the form of standard templates when new research findings, and evidenced based procedures, are adopted and utilized in the TIIPS display.

Based on the PDS Values, the computer is further programmed to calculate a Percentage Functioning Level for each subsystem (e.g., the system is functioning at "75% capacity"), and generate and display a TIIPS model visually and graphically incorporating the PFL.

In typical current medical practice, an experienced physician will weigh test results, and based on experience and judgment only, he/she will mentally assign a percentage functioning level to a particular subsystem. For example, a physician will request 3 tests of the renal system, and based on the totality of the results, will decide (based on judgment only) that the renal system is functioning at roughly 75% capacity.

To calculate and communicate this level of functioning within the TIIPS model, the physician will be provided with at least one electronic page to select tests and assign percentages to weigh the test results. The apparatus is programmed to automatically calculate a Percentage Functioning Level for each subsystem for which there is physician data, and display the PFL on the TIIPS model.

FIGS. 9A and 9B collectively show an exemplary Calculated Function Worksheet ("CFW") 24 for a physician to set PDS Values for a patient's renal subsystem. The physician sets PDS Values on the CFW for a particular patient. The apparatus is programmed to calculate a percentage functioning level ("PFL") for that particular subsystem based on physician-determined PDS Values. The apparatus is further programmed to graphically display the PFL as a certain percentage functioning level of the subsystem within the TIIPS model.

Referring again to FIGS. 9A and 9B, the CFW 24 may be provided to the physician on paper, but in the preferred embodiment is provided electronically as one of multiple CFW screen options in response to activation of the "Set PDS" icon in Quadrant C of the display 11 as shown in FIGS. 7 and 8. The CFW 24 includes a broad list of renal system-related tests and patient characteristics to take into account, not simply tests aimed at kidney function. This prompts the physician to think about tests or physical aspects about the patient he/she may not otherwise consider.

Referring to FIG. 9A, in the first left-hand column 9000 of the CFW 24, the physician selects the desired renal system-related tests for the patient. The second column 9005 lists the various tests available. In the third column 9010 labeled "Percentages Generated", each test is equally weighed (e.g., if 4 tests are ordered, each test is assigned a 25% weight). In the fourth column 9015 labeled "Percentages Assigned," the physician weighs the relative importance of the test results assigning percentages to each test with the total of the percentages equaling 100%. For example, if 4 tests were selected, but the physician felt that two of the tests were more important or more indicative of overall functioning for the subsystem, he/she could assign percentages of 40% and 30% to the more important tests, with 15% assigned to the other two tests, respectively. In the fifth column 9020 labeled "Normal Values," the normal ranges for the test results are preprogrammed into the system, and those ranges are displayed for the physician to see. The "Normal Values" 9020 are set by each institution and may differ from one hospital or laboratory to the next. In the sixth column 9025 labeled "Current Values," the actual test results are entered and displayed. In the seventh column 9030 labeled "Patient & Disease Specific Values," the physician enters a desired or target test result for the patient. In the eighth column 9035, labeled "Calculated Function," either the physician or the system compares the desired outcome (the PDS Value 9030) with the actual test outcome (the "Current Value" 9025) and assigns a percentage relative to the "Percentages Assigned" 9010 that corresponds to the percentage difference between the desired and actual outcome.

For example, a physician requests a BUN test from column 9005 and assigns a weighted percentage of 40% 9015 to the test results. The Normal Values 9020 for the test results are 7-23; the actual test result 9025 comes in at 12, and the assigned PDS Value 9030 is 12. The test results 9025 are in line with what the physician wanted to see, so the Calculated Function 9035 is 40%, matching the Percentage Assigned 9015.

As another example, a physician requests a Uric Acid test 9005 and assigns a percentage of 15% 9015 to the test results (indicating this particular test is not as important as other tests). The Normal Values 9020 for the test results are 2.4-6; the actual test result 9025 comes in at 4, and the assigned PDS Value 9030 is 3. The test results 9025 are higher than what the physician wanted to see, which is not desired. The Calculated Function 9035 is set at 10% as a result, which is below the 15% Percentage Assigned 9015. In other words, if the test results 9025 are poor in comparison to what the physician hopes to see (the PDS Value 9030), the Calculated Function 9035 is lower than the Percentage Assigned 9015; conversely, if the test results 9025 are better in comparison to what the physician hopes to see (the PDS Value 9030), the Calculated Function 9035 is higher but cannot exceed the level of the Percentage Assigned 9015.

The percentages listed in the Calculated Function column 9035 are then added up for a "Total Function" or Percentage Functioning Level ("PFL") representing the percentage capacity at which the renal system is operating in this particular patient. If the PFL is 75%, the patient's renal system is operating at 75% capacity. The computer is programmed to graphically represent the PFL on the TIIPS model 12 as a deteriorating arrow 26 aimed towards the central region 16 within the outer ridge 4.

In this manner, a physician is able to establish the PFLs for multiple subsystems. The physician also may enter 'fictitious' PDS Values and other data to see how the model 12 will change to predict how the patient will respond under specific circumstances.

FIGS. 9C through 9F show a sequence of exemplary graphic screen displays for an alternate embodiment for a CFW 50. A physician may prefer to set the PDS Values visually using the graphic system 50 shown in FIGS. 9C through 9F. The graphic CFW 50 provides a visual representation of each subsystem within the greater physical system. The graphic CFW 50 comprises a central region 16 representing failure of the subsystem and a series of concentric ridges 4 substantially centered about the central region 16. Each ridge 4 represents a level of function of the subsystem. However, instead of wedge shaped regions upon the ridges, the graphic CFW 50 comprises at least one adjustable percentage marker 52 extending from the center region 16 outward to the furthest ridge 4.

Figure 9C:
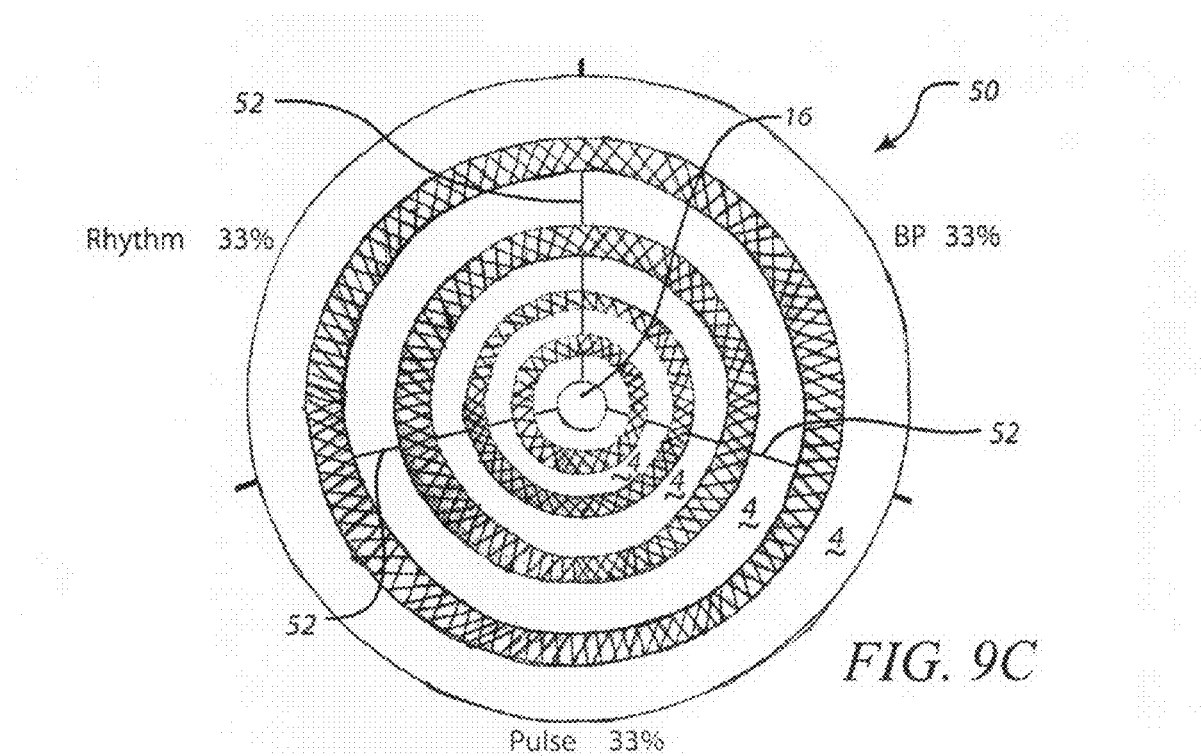
FIG. 9C is a photographic diagram of an exemplary graphic Calculated Function Worksheet showing equal percentages assigned to multiple tests, according to the invention.
Figure 9D:
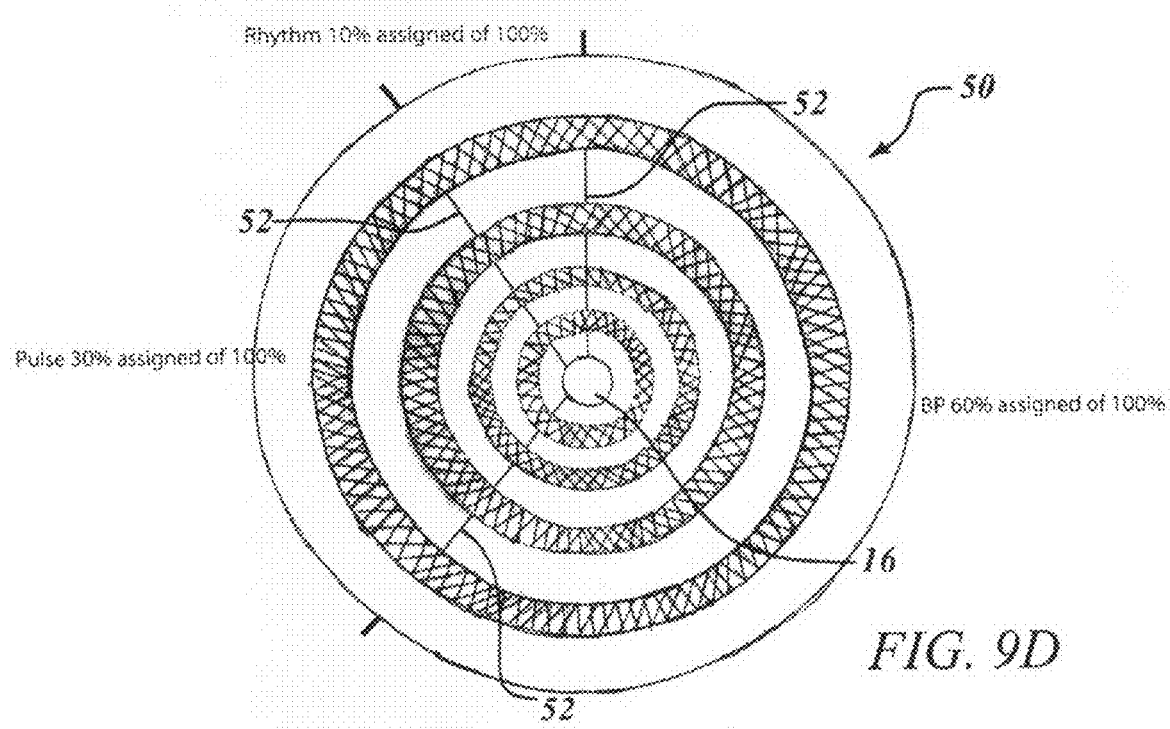
FIG. 9D is a photographic diagram of an exemplary graphic Calculated Function Worksheet showing weighted percentages assigned to multiple tests, according to the invention.

FIG. 9C graphically displays information from columns 9000, 9005 and 9010 of FIGS. 9A and 9B, namely, the subsystem tests selected by a physician, and the initial percentages assigned to each test representing 100% divided equally by the number of tests (33% for three tests). FIG. 9D graphically displays information from column 9015 of FIGS. 9A and 9B, namely, the weighted percentages assigned by the physician for each selected test. The apparatus is programmed to allow a physician to numerically enter the percentages, or to click and drag the percentage marker(s) 52 to desired position(s).

Figure 9E:
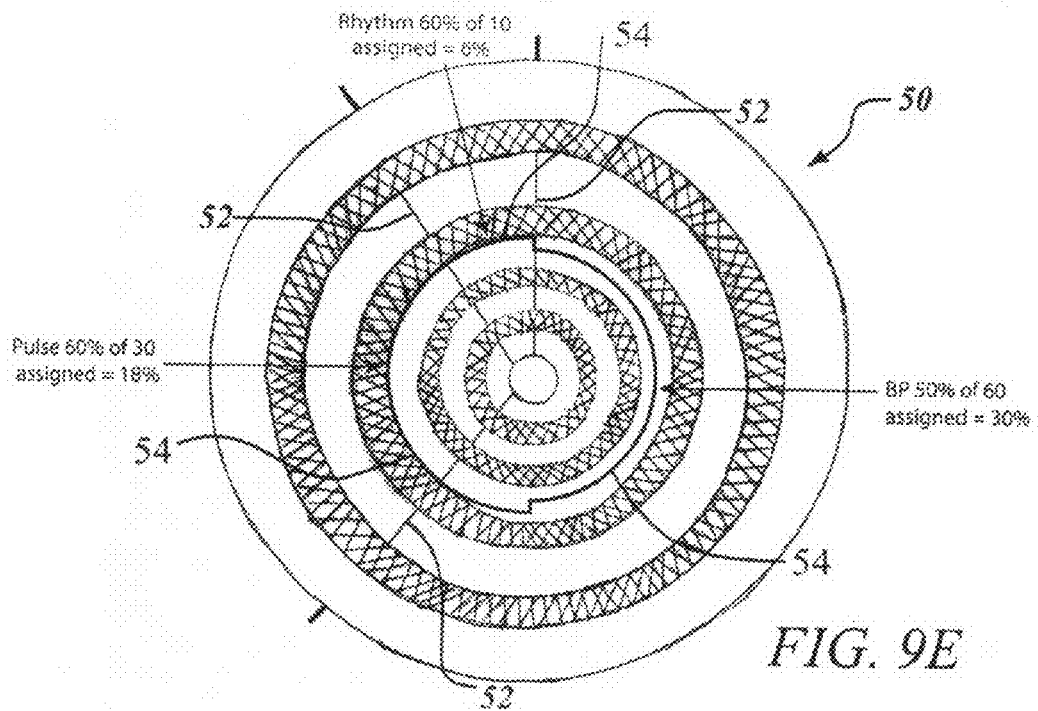
FIG. 9E is a photographic diagram of an exemplary graphic Calculated Function Worksheet showing PDS Values assigned to multiple tests, according to the invention.

FIG. 9E graphically displays information from column 9030 of FIGS. 9A and 9B, namely, the PDS Values. The PDS Values for each test are visually represented by PDS Value rings 54 on the ridges 4. The lower the PDS Value, the closer the ring 54 is located to the central region 16. The apparatus is programmed to allow a physician to numerically enter the PDS Values, such as on a keyboard, which are then represented by the rings 54 and/or to provide a user with the ability to click and drag the PDS Value rings 54 to desired positions. Future embodiments comprise electronic determination of PDS Values without physician input and automatic assignment of rings 54 at the specified positions.

Figure 9F:
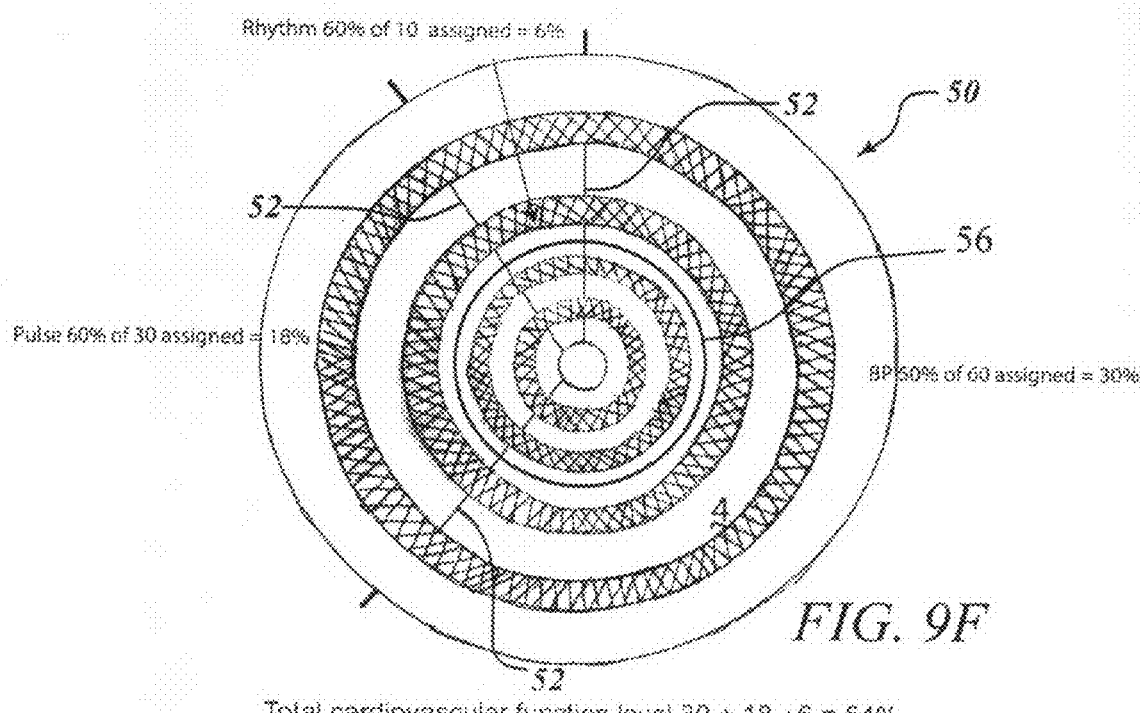
FIG. 9F is a photographic diagram of an exemplary graphic Calculated Function Worksheet showing the Percentage Functioning Level for the subsystem represented, according to the invention.

FIG. 9F graphically displays the overall Percentage Function Level from column 9035 of FIGS. 9A and 9B as a continuous circular ring 56. The exemplary PFL ring 56 shown in FIG. 9F is positioned approximately mid-way between the center region 16 and the outer ridge 4 to graphically represent a PFL of 54%.

It should be understood that any suitable or desired graphics may be utilized to represent the CFW 50 and allow a physician, or other user(s), to interact with the CFW 50 to determine a PFL, and that the exemplary graphics shown in FIGS. 9C through 9F are not limiting.

2) Exemplary Subsystem Mappings

Referring to FIGS. 9A and 9B, each subsystem has its own mappings comprising a list of tests and other medical considerations in column 9005 of a CFW 24. Tables 1-5 below list exemplary CFW mappings for the cardiovascular, endocrine, E&ENT, pain, musculoskeletal, infection and skin subsystems:

TABLE 1

| Cardio System Tests |
|---|
| Primary testing |
|   Cardiac Enzymes/Isoenzymes |
|     CK |
|     CK Isoenzyme |
|     LDH |
|     LDH Isoenzyme |
|   Troponin |
|   CRP-(C Reactive Protein) |
|   Lipid Panel |
|     Total Cholesterol |
|     HDL |
|     LDL |
|     VDRL |
|     Triglyceride |
|   CMP |
|   CBC |
|   Glucose, blood |
|   D-Dimer |
|   PT/INR |
|   PTT |
|   Digoxin Level |
|   BNP-Brain NatriureticPeptide |
| Secondary or Other Available Tests: |
| BMP |
|   Electrolytes |
|   LFTs |
|   GGT |
| Albumin, serum, urine, and 24 h urine |
|   Lidocaine Level |
|   Procainamide Level |
|   Quinidine Level |
|   Amiodarone Level |
|   Propranolol Level |
|   Disopyramide Phosphate |
|   Flecainide Level |
|   Mg |
|   ANA |
|   Antimyocardial Antibody |
|   TSH |
|   Thyroid Panel |
|   Sed Rate |
|   ABGs-Arterial Blood Gases |
|   Toxicity Screen |
| Other Diagnostic Testing |
|   ECG or EKG |
|   Echocardiogram |
|   Holter Monitor |
|   Cardiac Output |
|   Transesophageal Sonogram |
|   Electrophysiology Study |
|   CXR |
|   Stress Test |
|     Treadmill |
|     Adenosine |
|   Cardiac Catheterization |
|   PET Scan |

TABLE 2

| Endocrine System Tests |
|---|
| Primary testing |
|   HbA1C |
|   Fasting Blood Glucose |
|   2 hour Post-Prandial Glucose |
|   Glucose Tolerance Test |
|   TSH |
|   Thyroid Panel |
|     T3, free |
|     T3 RIA |
|     T3 RU |
|     T4 total (Thyroxine) |
|     Free Thyroxine Index (FTI) |
|   Thyroglobulin |
|   Thyroxine Binding Globulin |
|   Anti-Thyroid Antibodies |
|   Cortisol, fasting |
|   ACTH Stimulation Test |
|   Catecholamines |
|   DHEA |
|   Testosterone |
|     Free Testosterone |
|   FSH |
|   LH |
|   FSH/LH ratio |
|   Estrogen |
|   HCG |
|   PTH |
|   Calcitonin |
|   Calcium |
|   24 h Urine Calcium |
|   25-Hydroxy Vitamin D |

TABLE 3

| E&ENT System Tests |
|---|
| Primary testing |
|   CBC |
|   Hb |
|   HCT |
|   Viral Culture |
|   Gram Stain |
|   Culture and Sensitivity, specimen |
|   Fungal Culture |
|   Mono Spot |
|   Bleeding Time |
|   PT/INR |
|   PTT |
|   Thrombin Time |
|   Sed Rate |
|   Secondary Tests: |
|   Adenovirus Antibody Titer |
|   Adenovirus Immunofluorescence |
|   EBV Serology |
|   Chlamydia Culture |
|   Ocular Cytology |
|   Sjogren's Antibodies |
|   Biopsy and Histopathology |
|   Blood Culture |
|   Sputum Culture |
|   Bleeding Time |
|   Allergen-Specific IgE |
|   Mumps Antibody |
|   Anthropod Identification, specimen (Lice) |
|   Eosinophil Count |
|   Immunoglobulin E, serum |
|   Immunoglobulin A, serum |
|   HSV Antibody |
|   HSV Antigen |
|   Fluorescent Troporemal Antibody-Absorbed Double Stain Test |
|   (Syphilis Salicylate Level |
|   Other Diagnostics: |
|   Radiographs |
|   CT |
|   Visual acuity |

TABLE 3-continued

E&ENT System Tests

Slit Lamp Exam
Electromyogram and Nerve Conduction Studies
Hearing Tests
Tuning Fork Test of Weber, Rinne, and Schwabach Tests
Cerebral Angiogram

TABLE 4

Pain System Tests

Primary testing
  CBC
  CMP
  Blood Glucose
  Potassium
  Sodium
  Sed Rate
  Amylase
  Lipase
  UA
  CRP
  Platelet Count
Secondary Tests:
  Calcium, total serum
  Rheumatoid Factor-RF
  Sickle Cell Test
  Serotonin, plasma
  Thyroid Panel
  Uric Acid
  PT/INR
  PTT
Other Diagnostic Tests:
  Radiographs
  KUB
  US
  CT
  MRI
  Bone Scan
  Myelogram
  Thermography
  Pain Scale (different ones available)
  Quality of Life Scales (different ones available)

TABLE 5

Musculoskeletal System Tests

Primary testing
  CBC
  CMP
  CreatineKinase (CK)
  LDH
  Alkaline Phosphatase
  Sed Rate
  Uric Acid, serum and urine
Secondary:
  Calcium, total serum
  Calcium, urine
  Magnesium, serum
  PTH, serum
  Phosphorus, serum and urine
  25-Hydroxy Vitamin D
  Vitamin B1
  Joint Fluid Analysis
  Urine Fat
  Heavy Metals, blood and urine
  Mucin Clot Test
  Hydroxyproline, 24 hour urine
Other Diagnostics:
  Muscle Biopsy
  Radiographs
  CT
  MRI

TABLE 5-continued

Musculoskeletal System Tests

Bone Scan
Electromyogram and Nerve Conduction
DEXA

TABLE 6

Infection System Tests

Primary testing
  CBC
  CBC with Differential
  Sed Rate
  UA
  Gram stain (of site)
  Culture and Sensitivity
  Urine,
  Blood
  Sputum
  Wound
  Throat
  CSF
  Paracentesis fluid
  Joint fluid aspirate
  Stool
  other site
  HIV
Secondary or other tests:
  CRP
  VDRL or RPR (syphilis)
  Mono Spot
  Biopsy
  Bronchial Aspirate
  Histopathology
  Cytology
  Anerobic culture
  Fungal culture
  Viral culture
  CMV titer
  EBV titer
  HSV antibody/antigen
  *Mycobacterium* culture
  *Chlamydia* culture
  *Neisseriagonorrhoeae* culture
  *Bordetellapertussis* culture
  *Nocardia* culture
  Toxoplasmosis serology
  Rubella titer
  CSF culture and cytology
  ppd
  Viral Hepatitis serology
    HAV AbIgM
  HAV AbIgG
  Hep B Surface antigen
  Hep B Surface antibody
  Hep B Core AbIgM
  Hep B Core AbIgG
  Hep BE antigen
  Hep BE antibody
  Hep B DNA qualitative
  Hep B DNA quantitative
  Hep B genotype and mutations
  Hep C antibody
  *H. pylori* serum antibody
  *H. pylori* stool antigen
Other Diagnostics:
  CXR
  MRI
  CT
  Spinal Tap
  Sigmoidoscopy
  Cytoscopy
  Thoracentesis

TABLE 7

Skin System Tests

Primary testing
CBC
TSH
Sed Rate
Eosinophil Count
ANA
Anti-DNA Antibody
CRP
Lupus Panel
Immunoglobulin E
Allergen-Specific IgE
Ferritin
Iron Studies
   Serum Fe
   TIBC
   % Fe Sat
Platelet Count
MPV
Gram Stain
Culture and Sensitivity
Culture, Anaerobic
Culture, Fungal
Culture, Viral
HSV Antibody
Herpes Virus Antigen, specimen
Skin Scrapings for Ova, Mites
KOH Wet Mount Prep
Biopsy and Histopathology
Cytology, specimen
Secondary:
Blood Culture
Albumin, serum
Albumin/Globulin Ratio
Electrolytes
BUN/Creat
Osmolality, serum
Protein, serum
Chromium
Heavy Metals, blood and 24 h urine
Porphyrins, Quantitative, blood
Androstenedione
Dehydroepiandrosterone, Sulfate, serum, and 24 h urine
17-Hydroxycorticosteroids, 24 h urine
17-Hydroxyprogesterone
17-Ketogenic Steroids, 24 h urine
17-Ketosteroids, total and 24 h urine
Pregnanetriol, urine
Prolactin
Testosterone
   Total
   Free
LFTs
Bili, Total
Drug Toxicity Screen
Capilary Fragility Test
Platelet Antibody
HIV
Rubella Serology

TABLE 7-continued

Skin System Tests

Immunoglobulin M
Toxophasmosis, Rubella, CMV, HSV Serology (TORCH)
Rubeola Serology
Scleroderma Antibody
Occult Blood, urine
Skin Tests for Hypersensitivity
Varicella-Zoster Virus Serology
Rochalimaeahenselae Antibody
Genital *Bacillus* Culture for Haemophilusducreyl
Anthropod Identification
VDRL or RPR
Rocky Mountain Spotted Fever Serology
Trichinosis Serology
Other Diagnostic Tests:
CXR
Bone Marrow Biopsy 3) Exemplary Scenarios The following examples illustrate scenarios for assigning values and generating Percentage Functioning Levels which are then graphically represented on the subsystem wedges for the TIIPS model.

i) Young Healthy Traumatic Accident Scenario

Assume a 24 year old healthy male is in a ski accident. The mountain to hospital transport time is four hours. Witnesses reported a high speed solo accident without helmet. Upon arrival to the ER, the patient is poorly hydrated. His vital statistics are: BP 75/40 P 140 R 22 T 37.0 Glasgow Coma Scale 11. No obvious deformities. Spinal series negative, backboard removed. A cat scan reveals a pelvis fracture. A Foley is placed with initially 100 cc urine. Laboratory results are: Hct 36, Hb 12, creatinine 0.6, BUN 20, urine with 6-10 RBCs per HPF, +urobiligen, specific gravity 1.025. Vigorous fluid resuscitation is begun. The percentages assigned to the renal test results by the physician in this instance are:

Hourly urine output 40%

Blood in urine 30%

Specific gravity (important but not usually followed these days) 15%

Creatinine 15%

An exemplary CFW 24 for the renal system is as follows:

| Primary testing | Percentages generated | Percentages assigned | Normal values | Current values | P&DS values | Calculated function |
|---|---|---|---|---|---|---|
| Hourly urine output | 25 | 40 | 30 | 22 | 30 (Norm) | 32% |
| Blood in urine | 25 | 30 | Neg | Pos | Neg (Norm) | 10% |
| Specific Gravity/urine | 25 | 15 | 1.003-1.031 | 1.025 | 1.003-1.031 (Norm) | 13% |
| Creatinine | 25 | 15 | 0.6-1.2 | 0.6 ml | 0.6-1.2(Norm) | 15% |
| | | | | | PERCENTAGE FUNCTIONING LEVEL: | 70% |

Under this scenario, the Percentage Functioning Level of the renal system is 70% of normal. The TIIPS apparatus takes this PFL and initially assigns decreasing arrows to the 70% functioning level for the renal subsystem.

Moving to the cardiovascular system for the patient, the cardiac markers are:
Blood Pressure 60%
Pulse 30%
Rhythm 10% (but if it changes, such as becomes VT or VF, then its importance changes)
An exemplary CFW 24 for the cardiovascular system is as follows:

| Primary testing | Percentages generated | Percentages assigned | Normal values | Current values | P&DS values | Calculated function |
|---|---|---|---|---|---|---|
| BP | 33 | 60 | 110/70 | 75/40 | 110/70(Norm) | 30% |
| Pulse | 33 | 30 | 60-90 | 140 | 60-90(Norm) | 18% |
| Rhythm | 33 | 10 | SR | ST | ST(Norm) | 6% |
| | | | | | PERCENTAGE FUNCTIONING LEVEL: | 54% |

FIGS. 9C through 9F show a graphic CFW 50 corresponding to the above data. Under this scenario, the PFL of the cardiovascular system is 54% of normal. The TIIPS apparatus is programmed to receive this PFL and initially assign a decreasing arrow to the 54% functioning level for the cardiovascular subsystem (within the ridge representing the 40-60% level of functioning).

The patient is diagnosed with hypovolemic shock which is essentially low total blood volume inadequate to perfuse his vital organs. Although not visibly bleeding, he is losing blood from his vascular system as he is bleeding into his body cavity from his fractured pelvis, thereby "third-spacing" his blood. His urine output on insertion of the urinary catheter shows that the patient began with some dehydration probably from his vigorous athletic activity on a sunny day. The fluid he took in during his ski day has left via his skin rather than his urinary system. Upon giving the patient intravenous fluids in the ER, his urinary output increases. The attending physician would like a measurement of at least 30 cc each hour which represents that his kidneys are actually getting enough blood flow to keep them functioning without organ damage. Once hydrated and his blood pressure increases, his hourly urine measurement also increases. Of concern is the finding of blood in his urine. This could represent kidney parenchyma damage or damage to the urinary system related to the fracture damaging urinary soft tissue. This could be considered equivalent to collateral damage in a war zone. Specific gravity could be measured indicating the patient's degree of hydration and ability to concentrate urine appropriately. The creatinine measurement is normal as would be expected in a young healthy male with no history of kidney problems. This is not expected to change quickly in an acute scenario such as this.

On admission his diagnosis includes pelvic fracture (Musculo-Skeletal), concussion, and contusions (Neurological) which is the cause of the subsequent effects of other systems. Prior to addressing the root cause of the patient's problems, he must be stabilized and prevented from dying due to the hypovolemic shock.

FIG. 10A is an exemplary TIIPS display 12 for this patient graphically representing the above data along with status arrows for the Percentage Functioning Levels. Based on the data collected upon admission, the following initial Percentage Functioning Levels are assigned as graphically represented in each subsystem of FIG. 10A:

FEN (65%)—The patient was dehydrated to begin with before the accident. FEN showed as 65%, important but not serious.

MUS-SKEL (50%)—When the accident occurred, serious enough muscle and bone injury to put the patient at the amber level, hence Musculo-Skeletal at 50%.

PAIN (60%)—His pain reported at 60% based on a Pain Scale visual image.

NEURO (70%)—Upon assessment of his Neurological status, it is determined that he is at a Glasgow Coma Scale of alertness at 11, so his Neurological function is shown at 70%.
CARDIO (54%)—Assessment of his Cardiovascular function, shown above, places him at 54%.
RENAL (70%)—Assessment of his Renal function, shown above, places him at 70%.
FEN (80%)—To treat this patient and stabilize him prior to surgery to repair his fractured pelvis and deal with possible brain injury, the physician must first treat the shock. The physician starts by increasing the amount of blood volume by starting intra-venous fluids. This being done, the FEN function has improved to 80%.
HEMAT (60%)—By starting intravenous fluids and increasing blood volume, because of the bleeding in the pelvis, the physician dilutes the amount of oxygen carrying hemoglobin in the patient's Hematological system. The function now falls to 60%. This can be repaired by giving more blood to the patient, while assessing for other possible bleeding throughout his system, as in the spleen or the Hepatic (Liver) system. However, in a young and healthy patient; this may not be necessary since they can tolerate a lower hemoglobin level. The same scenario in an infant or elderly individual will show Hematological function at a much lower level of function.
HEMAT (80%)—After the patient is given blood, the physician sees improvement in the Hematological system.
RENAL (80%)—The renal function then improves as the Urine output increases.
MUS-SKEL (75%) The patient can now go to Surgery to repair his fractured pelvis.

FIG. 10B shows an exemplary TIIPS display 12 indicating the patient has been stabilized sufficiently to take to surgery and is now recovering. Improving status arrows are shown in the Renal and Mus/Skel subsystems. The patient is in the Recovery Room being monitored for an inflammatory response and post-operative infection.

ii) Older Chronic Disease Scenario

A second scenario involves a 64 year old female patient suffering from Insulin Dependent Diabetes Mellitus (IDDM) with Chronic Renal Insufficiency (poor Kidneys), Hypertension, and Hypercholesterolemia. The patient reports she has run out of medication and could not afford her pills. Her medications are: Lipitor, Lisinopril, Lasix, KCL, Verapimil, Insulin, and Xanax. She presents to the ER with weakness and fatigue, brought in by family when the patient would not get out of bed all day, had not eaten or taken in fluids all day. The patient is alert and oriented but fatigued. Her vital statistics are: BP180/110 P 120 R 16 T 37.0 F BMI 40. Lab tests show: WBC 5.6, HCT 30, Hb 10, BUN 60, creatinine 3.2, GFR 40. Urine showed cloudy specimen, +WBCs, +leukocytes, −RBCs, specific gravity 1.020, +protein (albumin). An EKG shows Atrial Fibrillation at 120. The patient is diagnosed with new onset Atrial Fibrillation with rapid ventricular rate. Also she has a probable Urinary Tract Inflammation, underlying IDDM, chronic renal insufficiency, HTN, and hypercholesterolemia. She has an anemia which is uninvestigated so it is unclear if it is a new onset such as GI bleed or pre-existing such as anemia of chronic illness relating to her renal insufficiency. A call to her Principal Care Physician (PCP) has been made.

The percentages assigned to the renal test results by the physician in this instance are:

Creatinine 50% (quick, easy way to access function immediately)

BUN 10% (varies with blood volume also, creatinine more specific)

GFR 20%

Urine protein 10% (with her creatinine and disease process the physician might assume that she has proteinuria)

Urine output 10%

Figure 10C:
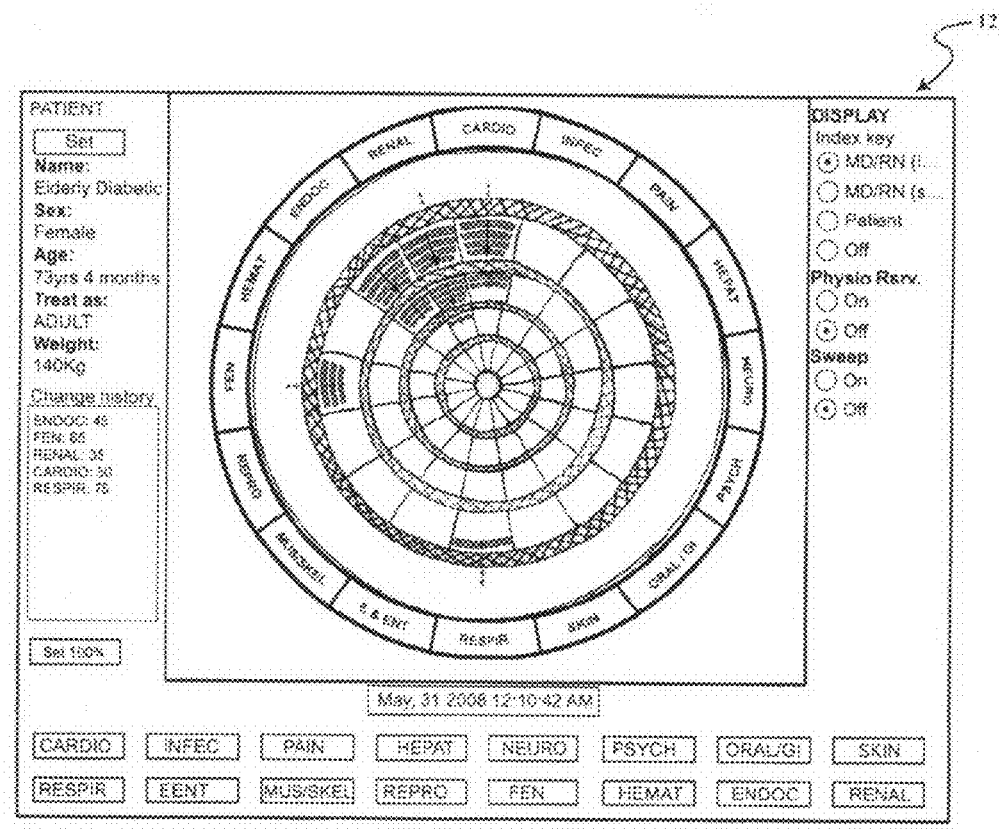
FIGS. 10C and 10D are photographic diagrams of exemplary TIIPS screen displays for an older diabetic patient scenario, according to the invention.

An exemplary CFW 24 for this patient's renal system is as follows:

FIG. 10C is an exemplary TIIPS display 12 for this patient graphically representing the above data along with status arrows for the Percentage Functioning Levels. As shown in FIG. 10C, this patient has adverse status arrows in the Endocrine, Renal, Cardio, Respiratory and FEN subsystems.

Figure 10D:
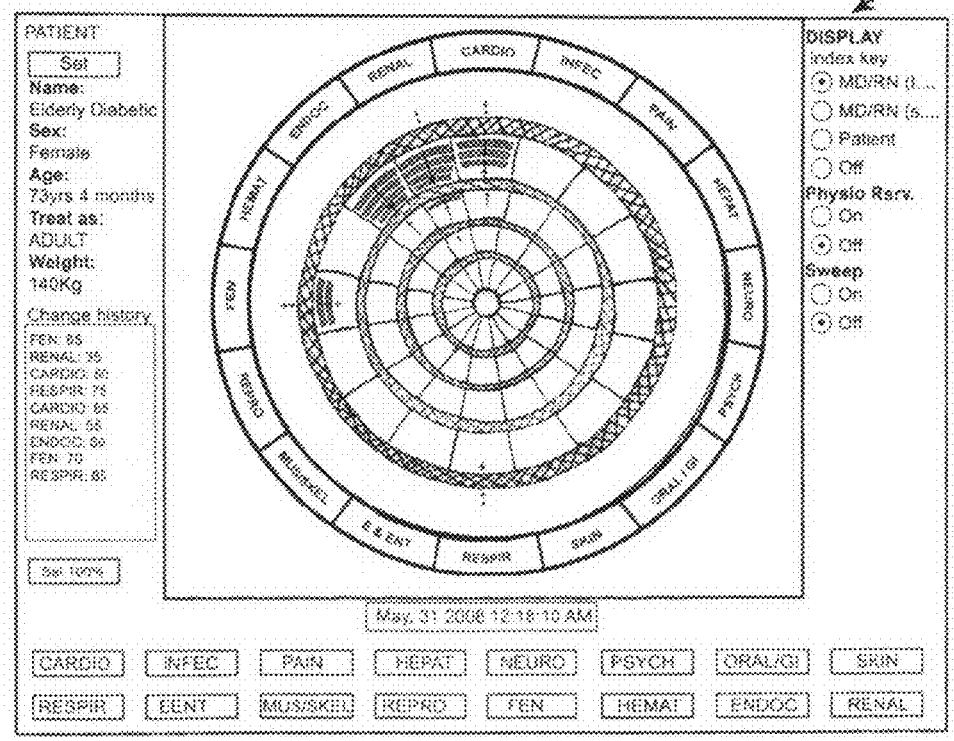

FIG. 10D is an exemplary TIIPS display 12 for the patient after she has been stabilized to the point where she can be given medication and food. This patient's values for BP and Pulse let us know that her Airway Breathing and Circulation parameters are intact and reflects that she has not taken her medication which is not surprising. The Rhythm strip and 12-Lead is what shows the onset Atrial Fibrillation, which is new. Once this patient is treated for the Atrial fibrillation and her heart (Cardio) is pumping effectively, the low nutrition status may be addressed. After she has been rehydrated (FEN), she can be given medicine to get her kidneys (Renal) functioning better and make sure her insulin is working well to improve her Endocrine function. As further shown in FIG. 10D, the patient's Respiratory system has improved, as graphically represented by status arrows pointing away from the central region.

4) Setting Function Level Based on Predispositions

The physician also may set a predisposition warning that affects the graphic display with respect to one or more subsystems. The predisposition warning may be set by manual input on a scale, or selection of a percentage decrease in functioning of the one or more subsystems, or other suitable

| Primary testing | Percentages generated | Percentages assigned | Normal values | Current values | P&DS values | Calculated function |
|---|---|---|---|---|---|---|
| Creatinine | 20 | 50 | 0.6-1.2 | 3.2 | 0.6-1.2 | 21% |
| BUN | 20 | 10 | 7-23 | 60 | 7-23 | 2% |
| GFR | 20 | 20 | >60 | 40 | >60 | 8% |
| Urine protein | 20 | 10 | neg | pos | neg | 1% |
| Urine output | 20 | 10 | 30 | 22 | 30 | 3% |
| | | | | | PERCENTAGE FUNCTIONING LEVEL: | 35% |

Moving to the cardiovascular system for this patient, the cardiac markers and weighted percentages assigned are:

Blood Pressure 20%

Pulse 20%

Rhythm 40%

12 Lead EKG 25%

An exemplary CFW 24 for this patient's cardiovascular system is as follows:

manner. The predisposition warnings are then displayed on the TIIPS model via flag icons located proximate the wedge region for the particular affected subsystem(s).

Figure 11A:
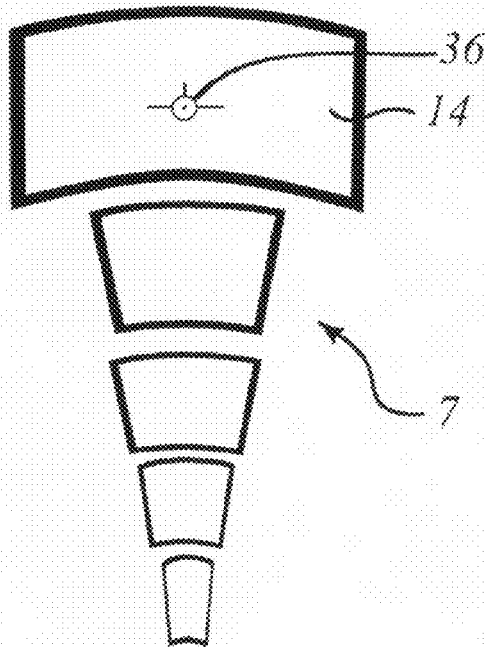
FIGS. 11A, 11B and 11C are close up partial view diagrams of a wedge-shaped subsystem with icons in the outer ring, according to the invention.
Figure 11B:
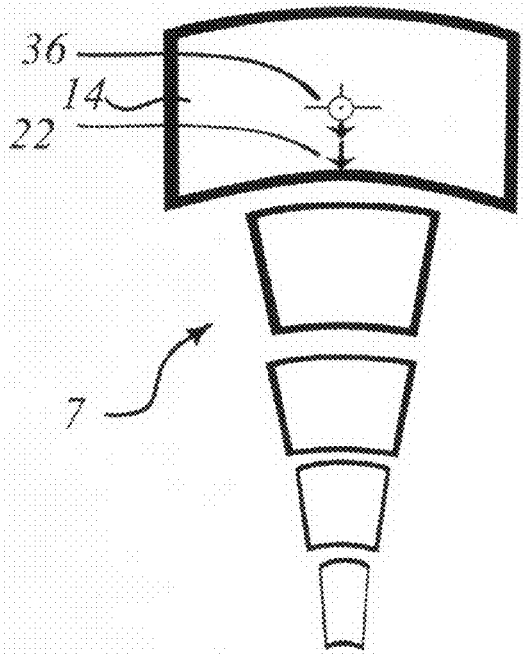
Figure 11C:
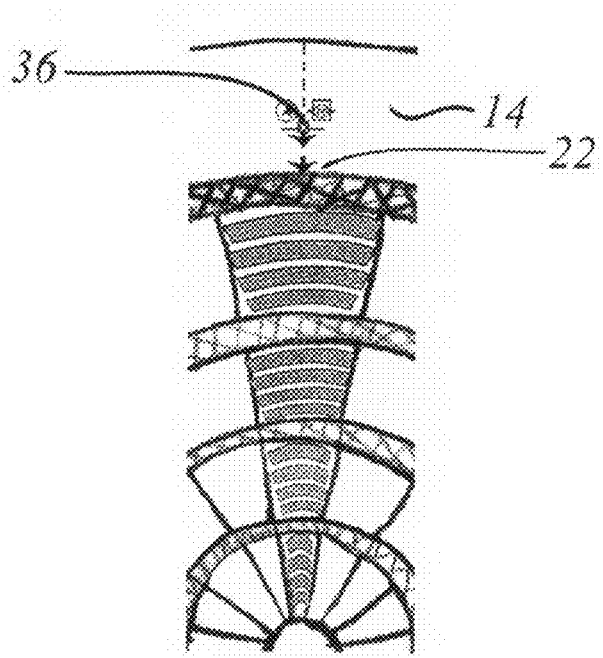

FIGS. 11A through 11C show exemplary flag icons 36 displayed in the outer ring 14 for a represented subsystem 7. The flags 36 shown in FIGS. 11A through 11C are centered above the wedge region 7 representing the patient's cardiovascular system (the wedge region 7 being a red color to

| Primary testing | Percentages generated | Percentages assigned | Normal values | Current values | P&DS values | Calculated function |
|---|---|---|---|---|---|---|
| BP | 25 | 20 | 120/75 | 180/110 | 130/85 | 12% |
| Pulse | 25 | 20 | 60-90 | 120 | 60-90 | 10% |
| Rhythm | 25 | 40 | SR | AF (50%) | 40 | 20% |
| 12 Lead EKG | 25 | 20 | SR | AF (50%) | SR | 10% |
| | | | | | PERCENTAGE FUNCTIONING LEVEL: | 52% | represent the cardiovascular system). The severity of the predisposition may be indicated by the position of the flags 36 within the outer ring 14, e.g., the closer the flag 36 in proximity to the outer ridge 4, the more severe the predisposition or more likely the predisposition will affect that subsystem's performance. The flags 36 are positioned at 5% increments within the outer ring 14, with 100% functioning represented by a flag 36 at the outer margin, with 5% decreasing functioning increments represented by the flag 36 being positioned closer to the first ridge 4. Arrows 26 also may be displayed to indicate trends in system performance.

Arrows 22 in the outer ring 14 graphically display infections. The infection arrows 22 are color coded to provide a viewer with additional information. For example, a white arrow signifies an infection of unknown origin. An infection of known origin may be color-coded for the subsystem (for example, a renal infection would be represented by a yellow-colored arrow 22). Likewise, the number of arrows may visually indicate whether the infection is primary or secondary in nature (single or double arrow). A secondary infection is shown by the double arrows 22 in FIGS. 11B and 11C.

Referring to FIG. 11A, a normal healthy person is assumed to have a cardiovascular system performing between 80 to 100% of normal function. However, if the patient has a family history of cardiovascular disease, the physician may fix the cardiovascular function at 90% as denoted by the flag 36. The predisposition may be based on family history, genetic markers, information from an Ethnic and Geographically Relevant Database, any other suitable source of information, or a combination thereof.

Referring to FIG. 11C, any suitable icon 36 may be utilized to draw the attention of a viewer to the predisposition and/or level of risk or decreasing function associated with that predisposition, along with other relevant icons. For example, FIG. 11C shows icons for a planned procedure (such as an upcoming surgery), and a special procedure on either side of the predisposition flag 36.

If a predisposition in one subsystem has the potential for affecting the performance of other subsystems, the TIIPS model may be programmed to automatically calculate and display icons relating to other subsystems and/or the physician may be prompted by the program to address those possibilities and set other icons for other subsystems.

5) Setting Physiologic Reserve

Physiologic reserve is the capacity of a patient to respond positively to physiologic disturbances. These disturbances include, but are not limited to, injury, acute illness (such as systemic infections), chronic illness (such as diabetes), system responses to medications (immunosuppressive drugs), cardio respiratory responses to anesthesia, and surgical interventions or manipulations. The TIIPS apparatus is programmed to provide a mechanism for the physician to assign a physiologic reserve setting which is incorporated into the displayed TIIPS model for that patient.

Referring to the young traumatic patient undergoing anesthesia to repair his fractured pelvis discussed in connection with FIGS. 10A and 10B, the induction of anesthesia further lowers the level of function of cardiovascular, respiratory, neurological, endocrine, renal, hepatic, hematological and infection systems, at the very least. Induction of anesthesia also deepens the gravity well, thus increasing the momentum of events that could lead to a worsening patient condition. However, this young man has 'elasticity' of his physiologic reserve system so that he will respond to the downward 'push' of anesthesia on the gravity well by resisting or even springing back to their baseline or above. The worsening condition is analogous to the surface of a trampoline which deepens with the gravitational force of a child, but pushes back and even up above the equilibrium state. Much of this resistance is mediated by automatic reflexes, some not yet identified, which lead to a patient's specific ability to return to baseline (the homeostatic response). Similarly, surgical intervention to repair the fractured pelvis will lower the functional level of several major body systems and push the gravity well deeper. However, the healthy young patient has the physiologic reserve to resist and even reverse the deepening of the gravity well.

Conversely, the physiologic reserve of the elderly diabetic patient with chronic renal failure discussed in connection with FIGS. 10C and 10D is significantly lower. This patient's baseline puts her in an even lower gravity well to start, and interventions related to induction of anesthesia (choice of medication, problems with airway management more difficult on an obese individual, depth of anesthesia, and other factors), will put her at an even lower gravity well. The risks with surgical interventions may have to be carefully weighed and may not be recommended. This patient may have very little physiologic reserve and so will have very little resistance to 'the downward push on the trampoline.' This lack of 'elasticity' may predispose the patient to a rapid deterioration should any minor complication arise.

In the TIIPS model 12, the overall average physiologic reserve is assigned by the physician and is graphically represented as a white concentric ring superimposed on the model 12 at a position representing a percentage physiologic reserve between 0 and 100%. Consequently, a ring representing 95% physiologic reserve would be positioned proximate the outer ring 14, whereas a ring representing physiologic reserve of 20% would be positioned proximate the center region 16. Any suitable or desired icon or graphic representation of physiologic reserve, or changes therein, may be utilized.

In an alternate embodiment, in addition to, or in lieu of, an overall physiologic reserve being assigned, a physiologic reserve is assigned for one or more subsystems 7 and is displayed in the model 12 at different percentage levels for different subsystems 7. The response of each subsystem 7 (Cardiovascular, Renal, Hepatic, etc.) distorts the gravity well at the local level, and, in this alternate embodiment, is individually displayed. Variations in the functional level of subsystems 7 and the reserve capacity of each subsystem 7 synergistically affect the overall function, either positively or negatively. The concept is akin to several children of heavy weights jumping on one side of a trampoline with fewer or lighter weighted children on the other side. Eventually, the dynamic forces may become so great that they will all coalesce in the middle and further deepen the gravity well, collectively. In the same manner, in a specific disease process, certain subsystems 7 may be more susceptible to improvements or failures than other subsystems 7. This could lead to improvement or a collapse of the overall system. The TIIPS apparatus is programmed to receive and analyze settings and/or data relating to the overall physiologic reserve of the patient and/or the physiologic reserve of individual subsystems 7 (akin to a local gravity well for that subsystem 7). As the TIIPS apparatus analyzes each lower level of data, the apparatus is more capable of capturing, dynamically, what is transpiring in an extremely complex entity. In this manner, the TIIPS model 12 has the ability to illustrate over real time, minor variations within local and sub local systems to truly reflect complex interactions.

6) Limiting Information Displayed

A physician (or other user of the apparatus) may desire that certain information not be displayed, such as the index for the TIIPS model 12, or the physiologic reserve ring discussed above. A physician may also want to view the TIIPS display 11 with fewer than all subsystems 7 shown. Accordingly, alternate embodiments allow for a user to turn off the display 11 of certain data and/or subsystems 7 otherwise graphically represented in the model 12. The apparatus is further programmed to alert a user to changes in any subsystem 7 regardless of whether that subsystem 7 is being displayed as part of the model 12.

b) Physician Use of PDAs

In practice, a physician may have remote access to the TIIPS model via a PDA with a screen display. The PDAs may be color-coded for identification purposes. For example, nurses' PDAs could be white; physicians' PDAs could be black; and family/advocate PDAs could be magenta in color. The PDAs could be further coded by striping, indicating specific rank or specialty within that institution. The PDA may be programmed to display both the TIIPS model and various icons linking to other data or functions of the PDA device. For example, an icon for the TIIPS model when activated may cause the PDA to display specific aspects of the TIIPS display for a particular patient; a medication icon when activated may provide the viewer with information regarding that patient's medications past and/or present; the telephone icon when activated may automatically call the patient's physician or bring up a menu of other persons/family members associated with the patient or patient's care team to whom direct calls could be made. In addition, the PDA will allow the physician to locate the patient by providing directions to the patient using built in GPRS. An assigned color, such as green, would indicate that the patient is within the range of the secure intranet.

c) Physicians Alerted to Infectious Disease

One of the greatest challenges for attending physicians is identifying and diagnosing infectious disease soon enough to save a patient's life. Bacterial infections are difficult to identify, and if left unchecked, lead to organ failure and death. A unique aspect of the TIIPS model is that it graphically displays neurological and endocrine reactions consistent with stress responses to bacterial infection. An experienced physician will recognize the stress response and address the possibility of a bacterial infection before it progresses too far.

d) Patient/Physician Interaction

Patients are often their strongest advocates and are increasingly educated about options and protocols given access to information available over the internet. Physicians at times have difficulty communicating all the risk factors involved in a particular course of treatment. Physicians may utilize the TIIPS model to illustrate to patients the complexity of their particular medical situation and illustrate possible outcomes if they follow a particular course of action by entering fictitious situational data into the model. In order to simulate the acquisition of patient data, the application is programmed to provide an icon for each body system that upon activation provides the viewer with a dialog box for that subsystem. The physician may then alter the data for that subsystem, including status level and predisposition settings. Upon completion of data manipulation, the TIIPS model is activated and both physician and patient may see the affect on the overall patient's life system.

In addition, for clarity and ease of patient/physician communications, the TIIPS model may be altered to display the subsystems by name in a circular index key showing the names of each body system against its corresponding wedge. An exemplary index key that could be used to interact with an adult patient would list the common/non-medical name of each subsystem: Blood Components, Hormones, Urinary System, Blood Circulation, Infection, Pain, Liver System, Brain, Psychological, Digestion, Skin, Breathing, Eyes, Ears, Nose & Throat, Musculo-Skeletal, Reproductive, Fluids Electrolytes Nutrition. The index may include more technical terms or be abbreviated, for example, for medical school teaching purposes. The index may be displayed in foreign languages; may be displayed in symbols universally understandable, or in words/symbols understandable by children in a pediatric medical setting.

5. Changes and Improvements to Apparatus Over Time

In addition to the situational data already discussed which updates the apparatus in real-time, the underlying mappings may be changed over time to reflect new information and new desired protocols for one or more subsystems.

a) Evidence Based Medicine

Moreover, if linked to the internet, the apparatus has the additional ability of providing Evidence Based Medicine. The practice of medicine is evolving away from journals and published papers, and towards a system of national or worldwide databases containing the newest information regarding medical advancements and studies. The "evidence" in these new databases is accessible over the internet and searchable by key word search programs. Companies are now offering hospitals updated information on areas of medicine via access to these databases.

One growing form of data available over the internet pertains to genetic predispositions and data regarding location-specific disease outbreaks, referred to herein as Ethnic and Geographically Relevant Data ("EGRD"). The TIIPS model is programmed to provide a physician access to the internet to search for EGRD for a particular patient and then integrate that data into the TIIPS model.

As an example, the apolipoprotein E (apoE) e2/e4 genotype has been found to be an accurate predictor of acute renal system malfunction after cardiac surgery. African American patients who carry the problematic allele are at risk of a 50% drop in renal function. This is further complicated by the fact that this drop in renal function is associated with a high rate of in-hospital mortality. Physicians utilizing the TIIPS model may query national research databases for such discoveries and match them with a patient's genetic profile thereby alerting the physician to the significant risk of a procedure such as Coronary Bypass or MVR (Mitral Valve replacement) surgery in this particular patient.

Likewise, a geographical query of a national or world-wide database by the physician may reveal that the patient was in an area where there was an outbreak of a Community Acquired MRSA (Methicilin Resistant Staplococcus A). Using the TIIPS model, a physician may query the location of such outbreaks and discuss with the patient whether he/she has been in those areas during an outbreak.

In an alternate embodiment, the computer would be programmed to automatically query databases upon entry of data regarding a particular patient and to alert the physician of any factors that may cause the physician to update the TIIPS model accordingly. The system would be programmed to mine databases and present the information to the physician and patient privately. The TIIPS model for each patient may be privately maintained by the hospital and/or patient.

b) System-Generated Improvements

In the preferred embodiment, the TIIPS apparatus is further programmed to undergo periodic statistical analysis of the situational data entered into the model over time for multiple patients. Following the statistical analysis, the model is programmed to alert users to the potential need to re-set mappings to better correlate with real-life situational data. For example, over time, significant situational data in the form of PDS Values assigned by physicians will be downloaded to the computer system. Eventually, the TIIPS apparatus will be able to predict and assign an appropriate PDS Value based on previous patterns of data entry.

Within each institution, once the TIIPS apparatus is established and real time data is collected, physicians will be able to make changes on policies and protocols based on what they learn from the TIIPS model. At a point in the future, the TIIPS apparatus will inform physicians of errors based on statistically relevant data analysis. Improved, more statistically valid parameters, will be set over time.

6. System Configuration

Figure 12:
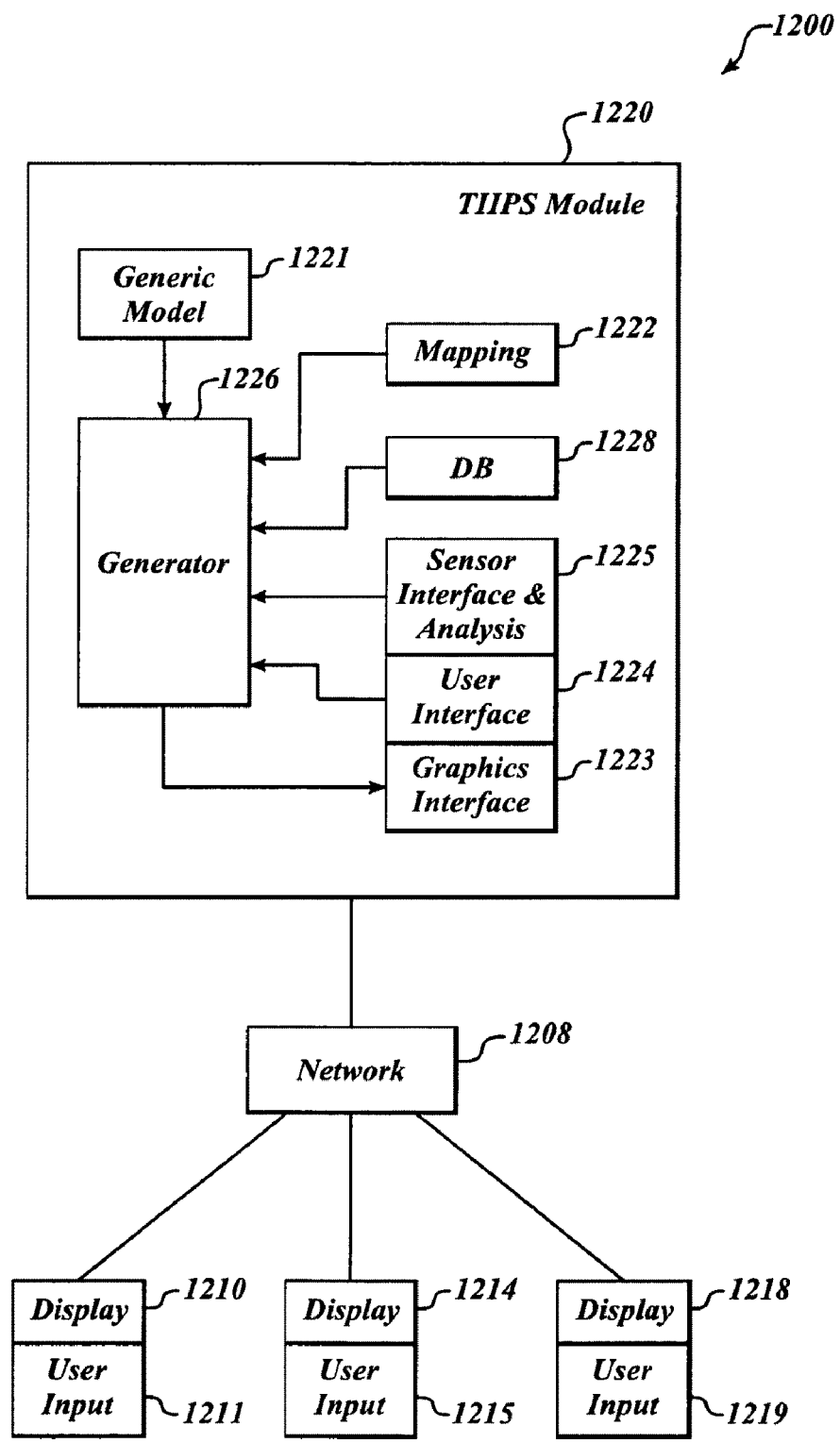
FIG. 12 is a block diagram of the configuration for a TIIPS apparatus, according to the invention.

FIG. 12 shows an exemplary block diagram for the TIIPS apparatus in operation 1200. Referring to FIG. 12, a generator application 1226 is programmed with the generic model 1221, mapping parameters 1222, and data from one or more databases 1228. The sensor interface 1225 comprises a first set of sensors to receive and analyze situational data, and a second set of sensors to receive and analyze data from at least one user interface 1224. In the medical application, the situational data comprises both measured data (from sensors attached to the patient) and calculated data. An example of measured data in the medical field is a measurement of a pulmonary arterial pressure using a catheter. Based thereon, and in conjunction with the Fick's principle (one of many methods), one may calculate cardiac output. Cardiac output is "calculated data."

Referring again to FIG. 12, the generator 1226 comprises an application program resident in at least one computer for receiving and analyzing any one or more of the following through a sensor interface 1225 and user interface 1224: measured data, calculated data, database information 1228 (such as ethnic and geographically relevant data), Percentage Functioning Levels based on Patient & Disease Specific values, predisposition warnings, and physiological reserve settings.

The sensor interface 1225 comprises a first set of sensors to receive and analyze situational data (collected via the prior art methods for monitoring and analyzing patient status), and a second set of sensors to receive and analyze data from at least one user interface. The data collected via the user interface includes the Percentage Functioning Levels for subsystems based on Patient & Disease Specific Values. The generator 1226 is programmed to continually compare the data received from the first set and second set of sensors against the mapping parameters 1222. Based thereon, the generator 1226 is programmed to generate and display the TIIPS model on an electronic screen display along with a graphics interface 1223 described in connection with FIGS. 7 and 8, discussed above.

Referring to FIG. 12, the generator program 1226 may be electronically separate for each patient or capable of connection to, and communication with, a network 1208 of other computers, PDAs, and the like. Multiple displays 1210, 1214, 1218 may be made available through the network 1208 to others in the patient care team, including nurses, physicians, and family members. External user input 1211, 1215, 1219 is optional with the level of input set for each team member, thereby allowing a physician more access than a patient advocate. The system may be operated wirelessly and/or through cable/fiber optic networks.

An alternate embodiment further comprises means for recording and storing one or more displays 1210, 1214, 1218 and the data generated by the generator 1226 over time. The screen displays and generator data 1226 may be recorded at least daily and the data securely stored for one or more future uses as discussed below.

7. Alternate Medical-Related Embodiments and Uses a) Quality of Care Analyses

The apparatus and system disclosed herein provides health care practitioners and persons assessing the quality of care within a health care setting with a pictorial representation over time of how a patient was treated. The manner in which a patient is treated depends significantly on the number and degree of underlying health issues and complications. Consequently, any appropriate assessment of quality of care requires analysis of not only simple statistics, such as survival rates, but also, an analysis of how well a health care system treated a patient given the number and complexity of underlying factors such as preconditions or complications. The system and apparatus disclosed herein may be utilized to more accurately assess quality of care by providing access to screen shots, over time, of the TIIPS display that takes into account all aspects of the patient's background and complications.

b) Captured Billing Practices

Currently, physicians spend significant amounts of time reviewing paper records of patient care to glean what procedures and other treatment steps were undertaken and to authorize billing in an attempt to capture those costs. Physicians are presented with little information about what happened with a particular patient when. Often, this results in delayed billing and missed costs that the hospital cannot recapture. The apparatus disclosed herein may be utilized to provide billing information in the form of screen shots, over time, representing the patient's status and the care given to the patient. As a result, costs may be visually identified and accurately billed with a record to support the billing.

c) Patient Records

The TIIPS system may further be utilized to provide patients with their own set of electronic medical records. The TIIPS screen shots and other data used to generate the TIIPS display may be electronically stored at one or multiple locations. The data may be downloaded to biometrically implanted chips, such as in the case of veterinary medicine, for immediate access. The electronic record may be shared over the internet, upon proper authorization, between health care institutions, such as in the case of a patient needing immediate care while traveling.

d) Long Distance Communications

The TIIPS display is further designed for use in providing remote medical services. For example, a medical professional working in a foreign, remote setting, may input data about a patient, generate an image, and send the image electronically to a hospital for analysis and consulting purposes. Both the physician on site, and a physician at the hospital could then view the same graphic and seamlessly communicate about the patient's condition.

e) Puzzle Model for Use in Remote Locations

The TIIPS model may be constructed as a 3-dimensional model, such as a magnetic "puzzle" model, to allow medical professionals in remote areas of the world where electronics are not accessible to physically move pieces of the model around to explain to the patient and/or family members the condition of the patient. The 3-dimensional model may be used to overcome the barriers of foreign language in remote areas of the world.

f) Game Application

The TIIPS model may be utilized as a game for children to play with. Essentially, the game involves a fictitious person getting sicker, and the child tries to save the patient. The game comprises the TIIPS model in a simplified electronic format appropriate for interaction by a child to treat a fictitious patient. Children would learn about what to do in case of an emergency and would learn about illnesses, recognition of illnesses, and treatment of diseases. Children exposed to the TIIPS model will have a greater understanding of the various subsystems within the human body and how they interact. Children may also have a better understanding of the physical results of obesity and poor nutrition and the resultant problems such as diabetes.

C. Aviation Application

The generic model 2 of the present invention may be utilized in the airline industry to assist pilots in preventing catastrophic accidents. The apparatus as applied to the aviation industry is referred to herein as the Totally Integrated Intelligent Flight Systems Display ("TIIFS"). Airline accidents often involve the same steps in a series of events leading to tragic results: 1) a catalyst event (such as mechanical errors in design or flaws in manufacturing of airplane parts); 2) a system fault (such as disregarding manufacturers' recommendations on inspections of parts); 3) a loss of situational awareness (such as a captain not being fully aware of the nature or cause of the mechanical problem); and 4) human error (such as the captain choosing to troubleshoot the problem while in flight as opposed to landing the plane as quickly as possible).

With regard to the human error factor, airline pilots may be prone to following the four steps that lead to accidents: namely: 1) posturing; 2) analyzing the facts to support a decision they have already made; 3) disregarding the advice or input of others; and, 4) persisting in a course of action despite a deteriorating condition due to loss of situational awareness.

Figure 13:
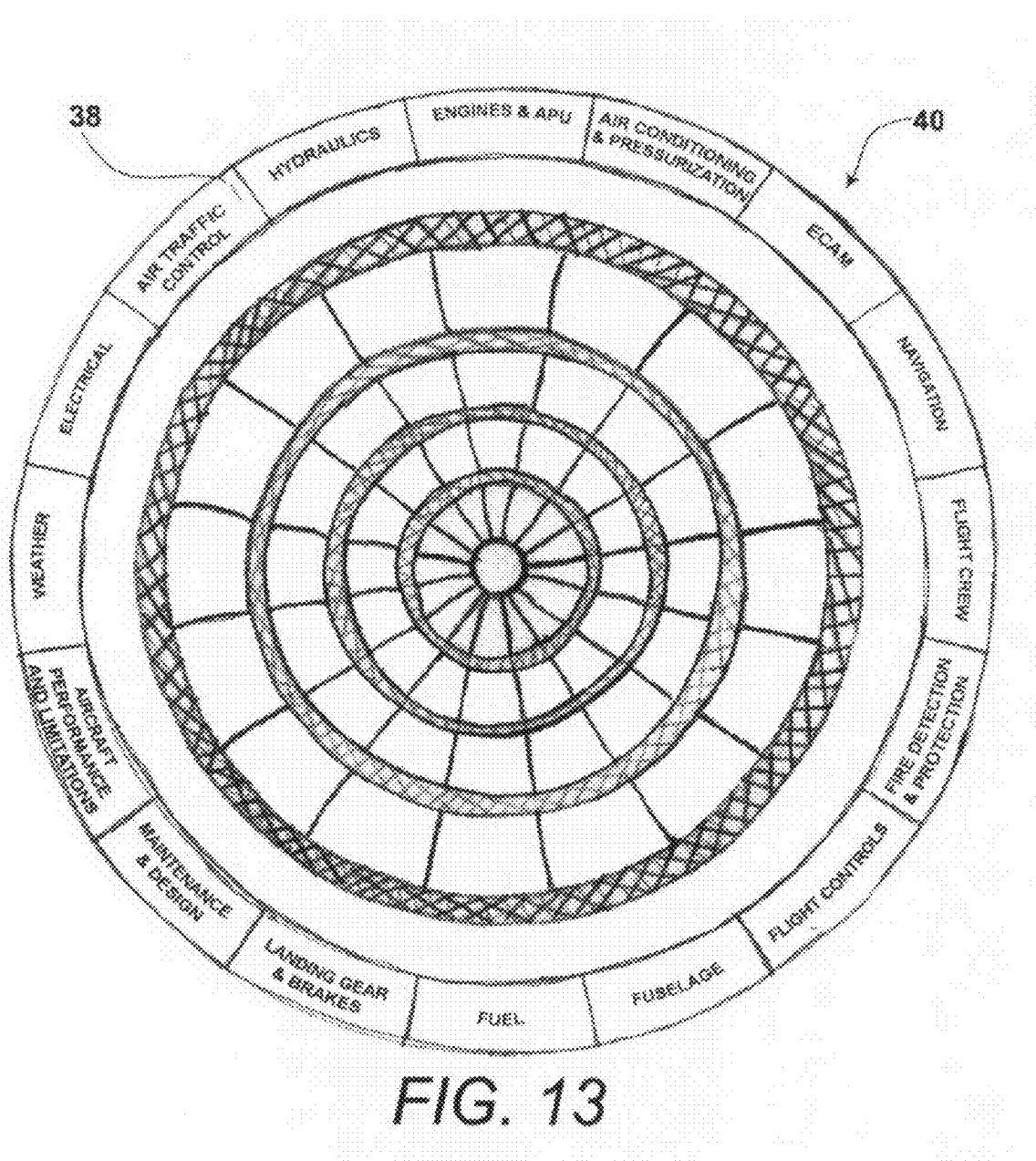
FIG. 13 is a photographic diagram of a top plan view of the TIIDS model applied to the aviation industry, according to the invention; and, FIG. 14 is a photographic diagram of a top plan view of the TIIDS model applied to the finance industry, according to the invention.

FIG. 13 is a diagram of an exemplary TIIPS display for monitoring the condition of an aircraft in operation. Specifically, the aircraft system as a whole is represented by: 1) a gravitational well having a central region representing destruction of the system (plane crash); 2) a series of concentric ridges substantially centered about the central region, where proximity of the ridges to the central region is representative of criticality of one or more subsystems to avoiding a plane crash; 3) wedge shaped regions upon the ridges extending outward from the central region representing various subsystems of the aircraft in operation, with each wedge being distinguished from the others by color or pattern or other distinguishing feature; and, 4) an icon representing the passage of time, where the color, position, shape and/or rotation of the icon represents prescribed analysis of the physical status of the aircraft being monitored.

Referring to FIG. 13, an index of color-coded subsystems similar to those applied in the medical application may be applied to the various subsystems of an aircraft in flight. Any desired number of color-coded subsystems may be monitored and displayed within the TIIFS model. An exemplary index of 16 subsystems for an aircraft comprises the following:

1. Fuel
2. Electrical
3. Engines and APU
4. Hydraulics
5. Navigation
6. ECAM
7. Landing Gear and Brakes
8. Flight Crew
9. Flight Controls/Autopilot
10. Air Conditioning and Pressurization
11. Weather
12. Fire Detection and Protection
13. Fuselage
14. Air Traffic Control
15. Aircraft Performance and Limitations
16. Maintenance and Design If problems develop in one system, the flight crew will be alerted on an on-going basis until the problem is resolved. Problems in one area/subsystem cannot be ignored while problems in another area/subsystem are being resolved. In addition to use of the model in real-time within the cockpit, the model may be used as a teaching device based on entry of fictitious data or entry of data gathered from a prior crash/disaster.

The TIIFS application is pre-programmed with mappings correlating to predetermined characteristics for each of the ridges and subsystems. In the preferred embodiment, the first (most outer) ridge represents functioning at an 80 to 100% level; the second ridge represents functioning at a 60 to 80% level; the third ridge represents functioning at a 40 to 60% level, and the fourth ridge represents functioning at the 20 to 40% level.

A sensor interface receives and analyzes measurements of the physical characteristics of the aircraft while in operation ("situational data"), as well as user input data from the cockpit, and a graphics generator prepares and displays an on-going presentation of the TIIFS model according to the physical characteristics and analysis from the sensor interface as correlated to the generic model by a selected one of the mappings. User input data may include data regarding the age and experience level of the aircraft's crew and may further assign a percentage functioning rate to the crew based on their most recent work activity. For example, if a crew has been flying for several days in a row, the system takes into account a percentage level decrease in functioning based on hypothetical crew fatigue.

Another example involves incidents relating to a fully loaded passenger Boeing 747 flying at night over the Pacific Ocean. One of the engines lost a slight amount of power and it resulted in drag on the left side of the aircraft. The autopilot then repositioned the rudder to turn the aircraft to the right to stay on course. The resultant drag created a loss of lift and the autopilot pitched the nose of the aircraft up to maintain altitude. This further increased drag and reduced lift. Unable to maintain the parameters set by the pilots, the forces programmed for the autopilot were exceeded, and it disconnected. The flight controls returned to the neutral position. The aircraft fell into a nose dive, and the forces experienced when trying to pull out of the dive were far greater than the mandated structural limits for a commercial airliner. As a testament to the Boeing 747, the crew was able to land the aircraft safely, but the aircraft was subsequently scrapped. TIIFS, if utilized in this scenario, would have given ample warnings to the crew to alert them of the position of the flight controls and pressures on the autopilot. These positions and pressures were totally inconsistent for the location of the flight at that point in time.

D. Finance Application

The generic model 2 of the present invention may be utilized in the financial industry to assist brokers in communicating with clients about clients' financial investments and changes thereto, and to assist private investors in monitoring their financial portfolios.

Figure 14:
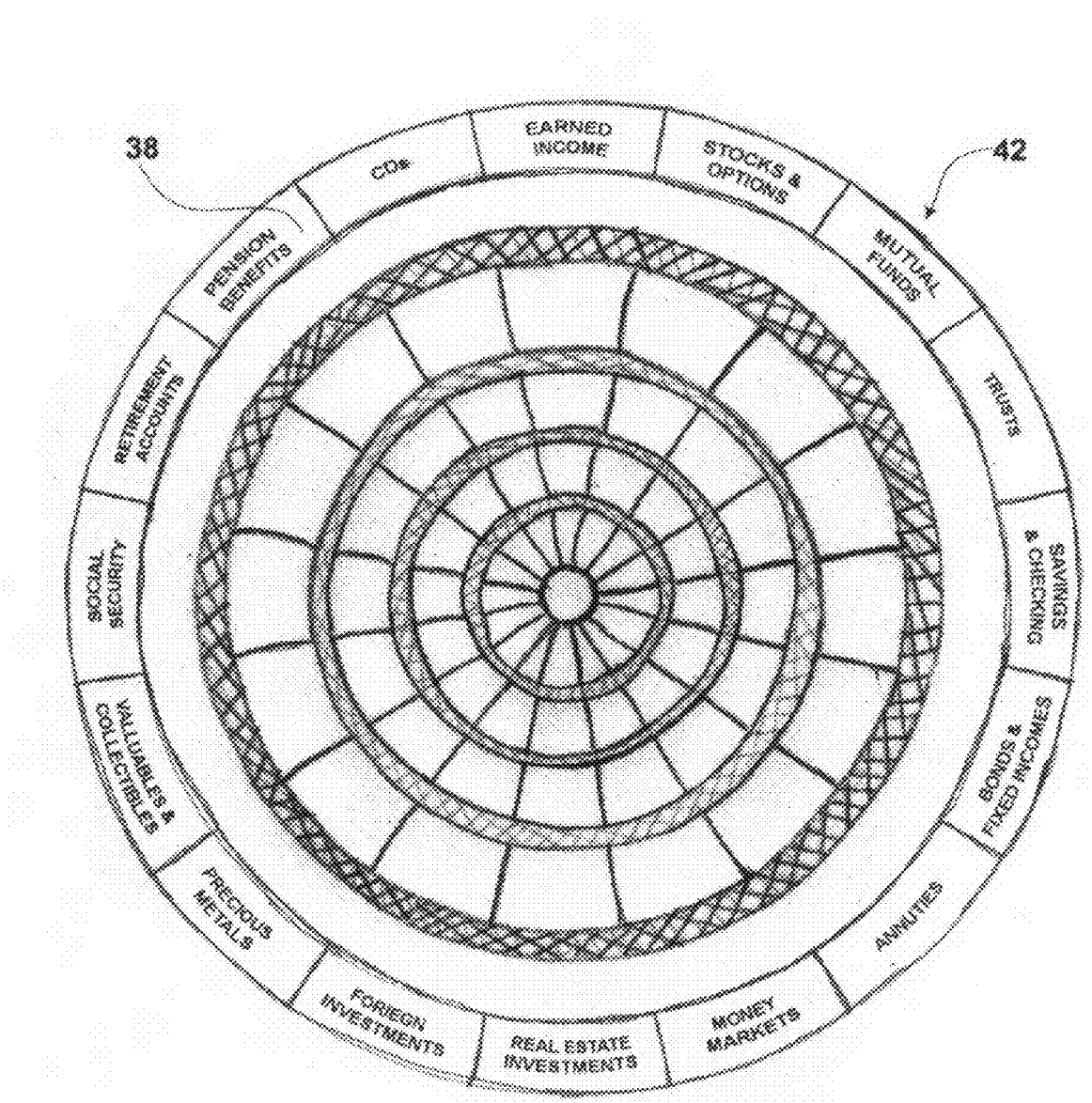

FIG. 14 shows an exemplary finance-related display with index 38 specific to the content of financial portfolios. The display graphically represents a physical system in the form of an electronic summary of a financial portfolio. The display is customized with information and subsystems applicable to investment management. Specifically, the portfolio as a whole is represented by: 1) a gravitational well having a central region representing destruction of the system (total loss/bankruptcy); 2) a series of concentric ridges substantially centered about the central region, where proximity of the ridges to the central region is representative of criticality of one or more subsystems to avoiding bankruptcy; 3) wedge shaped regions upon the ridges extending outward from the central region representing various sub-components of an existing portfolio, with each wedge being distinguished from the others by color or pattern or other distinguishing feature; and, 4) an icon representing the passage of time, where the color, position, shape and/or rotation of the icon represents prescribed analysis of the status of the portfolio being monitored.

Referring to FIG. 14, an index 38 of color-coded subsystems similar to those applied in the medical and aviation applications may be applied to the various sub-components of the portfolio. Any desired number of color-coded subcomponents may be monitored and displayed within the financial model. An exemplary index of 16 subcomponents for investment management comprises the following:
1. Earned Income
2. Stocks & Options
3. Mutual Funds
4. Trusts
5. Savings & Checking
6. Bonds & Fixed Incomes
7. Annuities
8. Money Markets
9. Real Estate Investments
10. Foreign Investments
11. Precious Metals
12. Valuables & Collectibles
13. Social Security
14. Retirement Accounts
15. Pension Benefits
16. CDs If losses are incurred in one subcomponent, the manager of the portfolio will be alerted by, for example, a change in the orbit and/or color of a ball icon in relation to the central region (i.e., an orbit in a ridge closer to the central region).

In addition to use of the model in real-time financial management, the model may be used as a teaching or learning device based on entry of fictitious data.

As with other applications based on the generic model, the finance application is pre-programmed with mappings correlating to predetermined characteristics for each of the ridges and subsystems. In the preferred embodiment, the first (most outer) ridge represents functioning at an 80 to 100% desired level; the second ridge represents functioning at a 60 to 80% desired level; the third ridge represents functioning at a 40 to 60% desired level, and the fourth ridge represents functioning at the 20 to 40% desired level.

A sensor interface receives and analyzes measurements of the performance of the various sub-components over time ("situational data"), such as streaming stock quotes, as well as user input data from the manager of the portfolio. A graphics generator prepares and displays an on-going presentation according to the data received from the sensor interface as correlated to the generic model by a selected one of the mappings. User input data may include data regarding the age and risk tolerance of the portfolio's beneficiaries/owners.

E. Petroleum Application

The generic model 2 of the present invention may be utilized in the petroleum industry to oversee and manage the operation of an oil drilling platform or other oil extraction and refining system. The display is customized with information and subsystems applicable to petroleum extraction and processing. Specifically, the system as a whole is represented by: 1) a gravitational well having a central region representing destruction of the system (e.g., explosion or fire); 2) a series of concentric ridges substantially centered about the central region, where proximity of the ridges to the central region is representative of criticality of one or more subsystems to avoiding destruction of the facility; 3) wedge shaped regions upon the ridges extending outward from the central region representing various sub-components of the system, with each wedge being distinguished from the others by color or pattern or other distinguishing feature; and, 4) an icon representing the passage of time, where the color, position, shape and/or rotation of the icon represents prescribed analysis of the status of the system being monitored.

An index 38 of color-coded subsystems similar to those applied in the medical, aviation and financial applications may be applied to the various sub-components of the system. Any desired number of color-coded subcomponents may be monitored and displayed within the petroleum model. An exemplary index of 16 subcomponents for petroleum extraction management comprises the following:
1. Fluid Catalytic Cracker
2. Delayed Coker
3. FCC Feed Hydrotreater
4. Vacuum Distillation
5. Crude Oil Atmospheric Distillation
6. Gas Processing
7. Hydrotreater ×4
8. Merox Treater ×2
9. Amine Treating
10. Hydrocracker
11. Isomerization Plant
12. Catalytic Reformer
13. Sour Water Steam Stripper
14. Gasoline Blending Pool
15. Claus Sulfur Plant
16. Asphalt Blowing
17. Hydrogen Synthesis
18. Alkylation If problems are incurred in one subcomponent, the manager of the system will be alerted by, for example, a change in the orbit and/or color of a ball icon in relation to the central region (i.e., an orbit in a ridge closer to the central region). As with other applications based on the generic model, the petroleum application is pre-programmed with mappings correlating to predetermined characteristics for each of the ridges and subsystems. In the preferred embodiment, the first (most outer) ridge represents functioning at an 80 to 100% desired level; the second ridge represents functioning at a 60 to 80% desired level; the third ridge represents functioning at a 40 to 60% desired level, and the fourth ridge represents functioning at the 20 to 40% desired level.

A sensor interface receives and analyzes measurements of the performance of the various sub-components over time ("situational data") as well as user input data from the subsystem operator(s). A graphics generator prepares and displays an on-going presentation according to the data received from the sensor interface as correlated to the generic model by a selected one of the mappings.

F. Vehicle Application

The generic model 2 of the present invention may be utilized in the automobile and trucking industries to provide a driver a visual display in real-time regarding the status of a vehicle in operation. The display is customized with information and subsystems applicable to the car, race car, truck, bus, or other vehicle being driven. Specifically, the vehicle system as a whole is represented by: 1) a gravitational well having a central region representing failure of the system to operate (loss of movement); 2) a series of concentric ridges substantially centered about the central region, where proximity of the ridges to the central region is representative of criticality of one or more subsystems to avoiding a break down of the vehicle; 3) wedge shaped regions upon the ridges extending outward from the central region representing various subsystems of the vehicle, with each wedge being distinguished from the others by color or pattern or other distinguishing feature; and, 4) an icon representing the passage of time, where the color, position, shape and/or rotation of the icon represents prescribed analysis of the status of the vehicle being monitored.

An index of color-coded subsystems similar to those applied in the medical, aviation, financial and petroleum applications is provided for the various sub-components of the system. Any desired number of color-coded subcomponents may be monitored and displayed within the vehicle model. An exemplary index of 16 subcomponents for a typical passenger car system in operation comprises the following:

1. Transmission
2. Steering and Suspension
3. Anti-Weather Devices
4. Anti-Theft Devices
5. Fuel
6. Passenger Entertainment
7. Supplemental Restraint
8. Air Conditioning
9. Braking System
10. Heating
11. Navigation System
12. Lighting
13. Engine
14. Electrical System
15. Instrumentation
16. Cooling System If problems are incurred in one subsystem, the driver of the vehicle will be alerted by, for example, a change in the orbit and/or color of a ball icon in relation to the central region (i.e., an orbit in a ridge closer to the central region). As with other applications based on the generic model, the vehicle application is pre-programmed with mappings correlating to predetermined characteristics for each of the ridges and subsystems. In the preferred embodiment, the first (most outer) ridge represents functioning at an 80 to 100% desired level; the second ridge represents functioning at a 60 to 80% desired level; the third ridge represents functioning at a 40 to 60% desired level, and the fourth ridge represents functioning at the 20 to 40% desired level.

A sensor interface receives and analyzes measurements of the performance of the various subsystems over time ("situational data"), and alternately, additional driver input data of information such as driver age, experience, weather conditions or the like. A graphics generator prepares and displays an on-going presentation according to the data received from the sensor interface as correlated to the generic model by a selected one of the mappings.

INDUSTRIAL APPLICABILITY

It is clear that the inventive Totally Integrated Intelligent Dynamic Systems ("TIIDS") model in this application for error prevention and management of complex systems has wide applicability to any industry involving complex systems at risk for catastrophic failure. The present invention provides a dynamic error model displaying readily visible information about the status and condition of complex systems over time.

OTHER EMBODIMENTS

The TIIDS model can be applied to the systems at work in the human body, in animals, an aircraft in flight, a ship on the high seas, an automobile, a government, a petroleum drilling platform or any other complex functioning system. The model has utility to any industry concerned with avoiding catastrophic errors, ranging from medicine, to insurance, to aviation. For example, in the hospital environment, the model may be utilized to oversee the status and needs of multiple patients, such as through providing thumbnail views of multiple patients on one screen. A person overseeing the hospital operations could view multiple models in real-time for Emergency Room patients to predict needs in the Operating Rooms and/or ICU, thereby allocating resources in a more timely and efficient manner. Also in the medical application, the models could be utilized to demonstrate procedures that were administered, and the reasons behind those procedures, to assist in billing for the care and/or establishing a basis for a disputed invoice. The model also has utility in overseeing and managing the operation of an on-going business enterprise, such as a casino with multiple revenue streams. As such, the exemplary applications disclosed herein are not limiting.

It should be understood that various modifications within the scope of this invention can be made by one of ordinary skill in the art without departing from the spirit thereof and without undue experimentation. For example, the barriers, both in the model and graphic CFW, may be visualized in any suitable manner, whether in cross-section, convex shape, concave shape, as rings, or any other shape or design. Likewise, the subsystems may be visually cued with any suitable colors, icons, or shapes. The model could comprise alerts to change via auditory signals or sounds at varying frequencies. The model could be programmed to unilaterally respond to barrier changes by automatic initiation of systems to counter-act system deterioration. The computer generating the model could be programmed to respond to barrier changes or other changes in the system by sending wireless communications to the viewer of the display, other person(s), and/or other computers. The person(s) monitoring the systems may be operating the systems themselves and/or overseeing the operation remotely.

This invention is therefore to be defined by the scope of the disclosure herein as broadly as the prior art will permit, and in view of the specification if need be, including a full range of current and future equivalents thereof.

I claim:

1. An apparatus for graphically displaying analytical data, comprising:
    a generic model to graphically represent a complex set of physical characteristics potentially leading to catastrophic failure of a physical system as follows:
        a depiction of wedge shaped regions extending outward from a central region, each wedge shaped region distinguished from others by color or pattern or other distinguishing feature, where the wedge shaped regions represent predetermined subsystems of the physical system;
        a series of concentric ridges overlapping the wedge shaped regions and substantially centered about the central region, where distance of each ridge from the central region represents functioning level as to the subsystems represented by the wedge shaped regions intersecting the ridge, and where greater distance of ridges from the central region indicates greater respective functioning levels;
        an icon depicting by color code an overall functioning level of the physical system, said icon selected from the group consisting of:
            an orb pulsating within the central region;

a rotating radar sweep extending from the central region, the sweep having an outer radius, said radius representative of a lowest failure bar for a subsystem with a lowest overall status level, said sweep rotating in a counter-clockwise direction when a most recent change in an overall status level is a decrease and rotating in a clock-wise direction at all other times;

a ball rotating in an orbit defined by two ridges, the proximity of the ball's orbit to the central region being representative of an overall status level for the physical system, said ball rotating in a counter-clockwise direction when a most recent change in an overall status level is a decrease and rotating in a clock-wise direction at all other times;

markers graphically depicting the functioning level of a subsystem by highlighting one or more of the ridges for a wedge shaped region;

one or more mappings, each mapping correlating predetermined characteristics of the physical system with the following in the generic model: functioning level represented by the ridges, subsystems of the physical system represented by the wedge shaped regions, overall functioning of the physical system represented in the icon;

a sensor interface to receive data including measurements of the physical characteristics of the physical system; and a graphics generator to prepare a presentation of the generic model according to the measurements of the physical characteristics as correlated to the generic model by a selected one of the mappings.

2. The apparatus of claim 1, wherein the series of concentric ridges comprise an outer first ridge, a second ridge, a third ridge and a fourth ridge, each ridge having an inner and outer radii corresponding to the following percentage function levels: 80 to 100 percent for the outer first ridge, 60 to 80 percent for the second ridge, 40 to 60 percent for the third ridge, and 20 to 40 percent for the fourth ridge.

3. The apparatus of claim 1, wherein the wedge shaped regions are color coded to correspond to a particular subsystem, are equally-sized, and form a full circle.

4. The apparatus of claim 1, wherein the markers comprise at least one status arrow superimposed upon one or more of the ridges.

5. The apparatus of claim 1, wherein the markers comprise at least one failure bar superimposed upon one or more of the ridges.

6. The apparatus of claim 1, wherein the generic model is displayed in two dimensions.

7. The apparatus of claim 1, wherein the generic model is displayed in three dimensions.

8. The apparatus of claim 1, wherein the sensor interface comprises sensors to receive and analyze situational data, and a user interface to receive and analyze updated operator input.

9. The apparatus of claim 1, wherein the graphics generator comprises an application program resident in at least one computer for generating and displaying at least one model on at least one electronic screen display.

10. The apparatus of claim 1, wherein the graphics generator comprises a graphics interface.

11. The apparatus of claim 1, wherein the physical system graphically represented is an airplane.

12. The apparatus of claim 1, wherein the physical system graphically represented is an electronic summary of a financial portfolio.

13. The apparatus of claim 1, wherein the physical system graphically represented is a petroleum extraction and refining apparatus.

14. The apparatus of claim 1, wherein the physical system graphically represented is a vehicle.

15. The apparatus of claim 1, wherein the physical system graphically represented is a business enterprise.

16. An apparatus for graphically displaying analytical data, comprising:

a generic model to graphically represent a complex set of physical characteristics potentially leading to a death of a human body as follows:

a depiction of wedge shaped regions extending outward from a central region, each wedge shaped region distinguished from others by color or pattern or other distinguishing feature, where the wedge shaped regions represent predetermined subsystems of the human body, and the central region represents death;

a series of concentric ridges overlapping the wedge shaped regions and substantially centered about the central region, where distance of each ridge from the central region represents functioning level as to the subsystems represented by the wedge shaped regions intersecting the ridge, and where greater distance of ridges from the central region indicates greater respective functioning levels;

an icon depicting by color code an overall functioning level of the human body, said icon selected from the group consisting of:

an orb pulsating within the central region;

a rotating radar sweep extending from the central region, the sweep having an outer radius, said radius representative of a lowest failure bar for a subsystem with a lowest overall status level, said sweep rotating in a counter-clockwise direction when a most recent change in an overall status level is a decrease and rotating in a clock-wise direction at all other times;

a ball rotating in an orbit defined by two ridges, the proximity of the ball's orbit to the central region being representative of an overall status level for the human body, said ball rotating in a counter-clockwise direction when a most recent change in an overall status level is a decrease and rotating in a clock-wise direction at all other times;

markers graphically depicting the functioning level of a subsystem by highlighting one or more of the ridges for a wedge shaped region;

one or more mappings, each mapping correlating predetermined characteristics of the human body with the following in the generic model: functioning level represented by the ridges, subsystems of the human body represented by the wedge shaped regions, overall functioning of the human body represented in the icon;

a sensor interface to receive data including measurements of the physical characteristics of the human body; and a graphics generator to prepare a presentation of the generic model according to the measurements of the physical characteristics as correlated to the generic model by a selected one of the mappings.

17. The apparatus of claim 16, wherein the one or more mappings comprise data represented on at least one calculated function worksheet.

18. The apparatus of claim 16, wherein a status level for the subsystem is represented as a percentage functioning level, said percentage functioning level calculated by assignment of at least one patient and disease specific value.

19. The apparatus of claim 16, wherein the sensor interface comprises a first set of sensors to receive and analyze situational data, said situational data comprising measured data and calculated data, and a second set of sensors to receive and analyze data from at least one user interface.

20. The apparatus of claim 16, wherein the graphics generator comprises an application program resident in at least one computer for receiving and analyzing any one or more of measured data, calculated data, ethnic and geographically relevant data, percentage functioning levels, predisposition warnings, physiological reserve settings.

21. The apparatus of claim 16, wherein the graphics generator comprises at least one graphics interface.

22. The apparatus of claim 16, wherein the model is constructed as a three-dimensional puzzle.

23. The apparatus of claim 16, wherein the model is utilized as part of an electronic game.

24. A computer implemented method of graphically displaying analytical data, comprising operations of:
  providing a generic model to graphically represent a complex set of physical characteristics potentially leading to catastrophic failure of a physical system as follows:
    a depiction of wedge shaped regions extending outward from a central region, each wedge shaped region distinguished from others by color or pattern or other distinguishing feature, where the wedge shaped regions represent conditions of predetermined subsystems of the physical system;
    a series of concentric ridges overlapping the wedge shaped regions and substantially centered about the central region, where distance of each ridge from the central region represents functioning level as to the subsystems represented by the wedge shaped regions intersecting the ridge, and where greater distance of ridges from the central region indicates greater respective functioning levels;
    an icon depicting by color code an overall functioning level of the physical system, said icon selected from the group consisting of:
      an orb pulsating within the central region;
      a rotating radar sweep extending from the central region, the sweep having an outer radius, said radius representative of a lowest failure bar for a subsystem with a lowest overall status level, said sweep rotating in a counter-clockwise direction when a most recent change in an overall status level is a decrease and rotating in a clock-wise direction at all other times;
      a ball rotating in an orbit defined by two ridges, the proximity of the ball's orbit to the central region being representative of an overall status level for the physical system, said ball rotating in a counter-clockwise direction when a most recent change in an overall status level is a decrease and rotating in a clock-wise direction at all other times;
    markers graphically depicting the functioning level of a subsystem by highlighting one or more of the ridges for a wedge shaped region;
  receiving one or more mappings, each mapping correlating predetermined characteristics of the physical system with the following in the generic model: functioning level represented by the ridges, subsystems of the physical system represented by the wedge shaped regions, overall functioning of the physical system represented in the icon;
  receiving data representing measurements of the physical characteristics of the physical system;
  operating a graphics generator to prepare a presentation of the generic model according to the measurements of the physical characteristics as correlated to the generic model by a selected one of the mappings.

25. The method of claim 24, where the received mapping constitutes a first mapping, and the operations further include graphically representing an entirely different physical system by receiving a second mapping and substituting the second mapping for the first mapping while retaining the generic model.

26. The method of claim 24, further comprising:
  receiving patient and disease specific (PDS) values signifying relative importance of some or all of the measurements of the physical characteristics of the physical system;
  applying the PDS values to the measurements of the physical characteristics of the physical system to compute a percentage functioning level (PFL) of one or more of the predetermined functional subsystems of the physical system;
  the graphics generator including graphical depiction of the PFLs in the presentation of the generic model.

27. The method of claim 24, where:
  the method further includes operations of receiving input including patient and disease specific (PDS) values signifying relative importance of some or all of the measurements of the physical characteristics of the physical system;
  the generic model further includes graphical features depicting a percentage functioning level (PFL) of one or more of the predetermined functional subsystems of the physical system;
  the mapping further operates to correlate predetermined characteristics of the physical system with the graphical features depicting the PFLs, where said correlation is conducted according to weighting specified by the received PDS values.

* * * * *